United States Patent
Bravo Gonzalez et al.

(10) Patent No.: US 10,226,430 B2
(45) Date of Patent: *Mar. 12, 2019

(54) DELAYED RELEASE DRUG FORMULATION

(71) Applicant: TILLOTTS PHARMA AG, Rheinfelden (CH)

(72) Inventors: Roberto Carlos Bravo Gonzalez, Binningen (CH); Thomas Buser, Nuglar (CH); Frederic Jean-Claude Goutte, Schwoben (FR); Abdul Waseh Basit, Middlesex (GB); Felipe Jose Oliveira Varum, Basel (CH); Ana Cristina Freire, Northampton (GB)

(73) Assignee: TILLOTTS PHARMA AG, Rheinfelden (CH)

( * ) Notice: Subject to any disclaimer, the term of this patent is extended or adjusted under 35 U.S.C. 154(b) by 156 days.

This patent is subject to a terminal disclaimer.

(21) Appl. No.: 14/397,977

(22) PCT Filed: Apr. 29, 2013

(86) PCT No.: PCT/EP2013/058921
§ 371 (c)(1),
(2) Date: Oct. 30, 2014

(87) PCT Pub. No.: WO2013/164315
PCT Pub. Date: Nov. 7, 2013

(65) Prior Publication Data
US 2015/0125525 A1    May 7, 2015

Related U.S. Application Data

(60) Provisional application No. 61/640,217, filed on Apr. 30, 2012.

(30) Foreign Application Priority Data

Apr. 30, 2012 (EP) ..................... 12166110

(51) Int. Cl.
| A61K 31/616 | (2006.01) |
| A61K 9/28 | (2006.01) |
| A61K 31/606 | (2006.01) |
| A61K 9/00 | (2006.01) |
| A61K 47/32 | (2006.01) |
| A61K 47/36 | (2006.01) |
| A61K 31/196 | (2006.01) |
| A61K 47/38 | (2006.01) |
| A61K 9/20 | (2006.01) |

(52) U.S. Cl.
CPC .......... *A61K 9/2886* (2013.01); *A61K 9/0053* (2013.01); *A61K 9/2013* (2013.01); *A61K 9/2054* (2013.01); *A61K 9/284* (2013.01); *A61K 9/286* (2013.01); *A61K 9/288* (2013.01); *A61K 9/2846* (2013.01); *A61K 9/2853* (2013.01); *A61K 9/2866* (2013.01); *A61K 9/2893* (2013.01); *A61K 31/196* (2013.01); *A61K 31/606* (2013.01); *A61K 31/616* (2013.01); *A61K 47/32* (2013.01); *A61K 47/36* (2013.01); *A61K 47/38* (2013.01)

(58) Field of Classification Search
None
See application file for complete search history.

(56) References Cited

U.S. PATENT DOCUMENTS

| 5,422,121 | A | 6/1995 | Lehmann et al. |
| 9,364,440 | B2 * | 6/2016 | Bravo Gonzalez .. A61K 9/2846 |
| 9,814,681 | B2 * | 11/2017 | Oliveira Varum ... A61K 9/2846 |
| 2003/0035839 | A1 * | 2/2003 | Hirsh ................... A61K 9/0056 424/471 |
| 2004/0028737 | A1 | 2/2004 | Deshpande et al. |
| 2007/0243253 | A1 | 10/2007 | Basit et al. |
| 2008/0193531 | A1 * | 8/2008 | Hermelin ............. A61K 9/2013 424/474 |
| 2010/0055173 | A1 * | 3/2010 | Penhasi ................ A61K 9/2013 424/452 |
| 2014/0056980 | A1 | 2/2014 | Oliveira Varum et al. |

FOREIGN PATENT DOCUMENTS

| WO | 96/36321 | * | 11/1996 |
| WO | 2008/135090 | | 11/2008 |

OTHER PUBLICATIONS

Sigma-Aldrich (accessed Jan. 28, 2018, 1 page, https://www.sigmaaldrich.com/catalog/product/aldrich/435228?lang=en&region=US&gclid=EAlalQob ChMlgdWxrYv22AlV1TaBCh15cQx IEAAYASAAEgJBcf D_BwE).*

Masataka Katsuma, et al., "Studies on lactulose formulations for colon-specific drug delivery", International Journal of Pharmaceutics, 249 (2002), pp. 33-43.

(Continued)

*Primary Examiner* — Alma Pipic
(74) *Attorney, Agent, or Firm* — Oblon, McClelland, Maier & Neustadt, L.L.P.

(57) ABSTRACT

Delayed release of a drug to the colon is achieved from a delayed release formulation comprising a core and a coating for the core. The core comprises a drug and the coating comprises an inner layer and an outer layer. The outer layer comprises a mixture of a first polymeric material which is susceptible to attack by colonic bacteria, and a second polymeric material which has a pH threshold at about pH 5 or above. The inner layer comprises a third polymeric material which is soluble in intestinal fluid or gastrointestinal fluid, said third polymeric material being selected from an at least partially neutralized polycarboxylic acid and a non-ionic polymer. In embodiments in which the third polymeric material is a non-ionic polymer, the inner layer comprises at least one of a buffer agent and a base. Advantages of formulations according to the present invention include accelerated release of the drug when exposed to colonic conditions and reduction or elimination of a food and/or alcohol effect on drug release after administration.

33 Claims, 8 Drawing Sheets

(56) References Cited

OTHER PUBLICATIONS

Fredrick Esseku[1,2], et al., "Bacteria and pH-Sensitive Polysaccharide-Polymer Films for Colon Targeted Delivery", Critical Reviews™ in Therapeutic Drug Carrier Systems, 28(5), 395-445 (2011).
U.S. Appl. No. 14/398,005, filed Oct. 30, 2014, Bravo Gonzalez, et al.

\* cited by examiner

DELAYED RELEASE DRUG FORMULATION

The present invention relates to a delayed release formulation with a core comprising a drug and a delayed release coating. In particular, it relates to a delayed release formulation for delivering a drug to the colon.

The targeting of drugs to the intestine is well known and has been known for over one hundred years. Commonly, the target of the drugs is the small intestine although the colon can be utilised as a means of achieving local therapy or systemic treatment. The requirements for the coatings on the drugs are different depending on the target site. In order to reach the colon, it is necessary for the drugs to pass through the small intestine, and therefore it is a requirement that a delayed release coating intended to release the drug in the colon does not release the drug in the small intestine.

Coated products for release in the small intestine commonly use polymer coatings which dissolve or disintegrate in a pH dependent manner. In the low pH environment of the stomach, the polymer coating is insoluble. However, on reaching the small intestine, the pH rises to 5 and above and the polymeric coating dissolves or disintegrates. A commonly used coating is one containing ionizable carboxylic groups. At higher pH levels, the carboxylic groups ionize, allowing the polymer coatings to disintegrate or dissolve. Common polymers of this type which are used include Eudragit® L and Eudragit® S.

Various methods of improving the release in the small intestine by ensuring an earlier release of the drug are known. US2008/0200482 is one of a number of references which discloses partially neutralizing the carboxylic groups in order to reduce the pH at which disintegration occurs. WO2008/135090 discloses a tablet with an inner coat of partially neutralized material and an outer coat with less or no neutralization. This is said to result in disintegration at an earlier time point when transferred from the stomach.

Release of drugs in the colon typically requires an alternative approach. The colon is susceptible to a number of disease states, including inflammatory bowel disease, irritable bowel syndrome, constipation, diarrhea, infection and carcinoma. In such conditions, drug targeting to the colon would maximise the therapeutic effectiveness of the treatment. The colon can also be utilised as a portal for the entry of drugs into the systemic circulation. Various formulations have been developed for colonic drug delivery, including pro-drugs as well as formulated dosage forms, with the latter being more popular since the concept once proved can be applied to other drugs.

The higher bacterial population in the colon has also been exploited in developing colonic drug delivery dosage forms through the use, as carrier materials, of naturally occurring polysaccharides that constitute substrates for the numerous enzymes of the resident colonic bacteria. These materials are able to pass through the upper gastrointestinal regions intact but are digested upon entry into the colon. Those studied so far include amylose, pectin, chitosan and galactomannan.

Amylose is resistant to digestion by the enzymes of the upper gastrointestinal tract. It is, however, fermented in the colon by α-amylase enzymes produced by over half of the 400 bacteria species resident in the colon.

One major attraction of using polysaccharides in this bacterial enzyme approach to colonic drug delivery is that materials used are of food grade and so would be safe for use in humans. They are usually applied as coatings or incorporated in the core material as a matrix carrier, and their digestion on entry into the colon by the colonic bacterial enzymes leads to the release of the drug load. An example of such a formulation, which employs an amylose coating, is disclosed in EP0343993A (BTG International Limited).

A major limitation with these naturally occurring materials, however, is that they swell excessively in aqueous media leading to leaching of the drug load in the upper gastrointestinal regions. To circumvent this problem, the naturally occurring materials have been utilised in a mixture with various impermeable materials.

EP0502032A (British Technology Group Ltd) teaches the use of an outer coating comprising a film forming cellulose or acrylate polymer material and amorphous amylose for a tablet comprising an active compound. The polymer material used is a pH independent release polymer material.

An article in Journal of Controlled Release (Milojevic et al; 38; (1996); 75-84) reports the results of investigations concerning the incorporation of a range of insoluble polymers into an amylose coating in order to control amylose swelling. A range of cellulose and acrylate based co-polymers are assessed, and a commercially available ethyl cellulose (Ethocel®) is found to control the swelling most effectively. A pH dependent soluble coating of Eudragit® L100 is employed but only in a multi-layer system comprising a bioactive coated with an inner coating of amylose and then an outer coating of Eudragit® L100.

A further amylose-based coating composition is disclosed in WO99/21536A (BTG International Limited). The coating composition comprises a mixture of amylose and a water insoluble pH independent film-forming polymer which is formed from a water-insoluble cellulosic or acrylate polymer material.

WO99/25325A (BTG International Limited) also discloses a delayed release coating comprising amylose and (preferably) ethyl cellulose or alternatively an insoluble acrylate polymer. The coating composition also includes a plasticiser and the method finds particular application in the preparation of dosage forms comprising active materials that are unstable at temperatures in excess of 60° C., as the composition is formed at lower temperatures than this.

WO03/068196A (Alizyme Therapeutics Ltd) discloses a specific delayed release coating for the bioactive prednisolone sodium metasulphobenzoate comprising glassy amylose, ethyl cellulose and dibutyl sebacate.

The use of polysaccharides other than amorphous amylose in a delayed release coating is disclosed in GB2367002 (British Sugar PLC). Examples include guar gum, karaya gum, gum tragacanth and xanthan gum. Microparticles of these polysaccharides are dispersed in a water-insoluble film-forming polymer matrix formed for example from a cellulose derivative, an acrylic polymer or a lignin.

WO01/76562A (Tampereen Patenttitoimisto Oy) discloses a peroral pharmaceutical formulation containing a drug and a chitosan (a polysaccharide obtained from chitin) for controlling its release. The drug and the chitosan are mixed into a homogeneous mechanical powder mixture which is granulated and then optionally tabletised. The granulation may be performed with an enteric polymer (such as a copolymer of methacrylic acid) or the granules may be provided with a porous enteric coating.

WO2004/052339A (Salvona LLC) discloses a pH dependent drug release system which is a free-flowing powder of solid hydrophobic nano-spheres comprising a drug encapsulated in a pH-sensitive micro-sphere. The nano-spheres are formed from the drug in combination with a wax material, and the pH-sensitive micro-sphere formed from a pH-sensitive polymer (such as a Eudragit® polymer) in combination with a water-sensitive material such as a polysaccharide.

An article in the European Journal of Pharmaceutical Sciences (Akhgari et al; 28; Mar. 2006; 307-314) reports the results of investigations into the use of certain polymethacrylate polymers to, inter alia, control the swelling of inulin. The polymethacrylate polymers tested were Eudragit® RS; Eudragit® RL; 1:1 mixtures of Eudragit® RS and Eudragit® RL; Eudragit® FS; and 1:1 mixtures of Eudragit® RS and Eudragit® S.

U.S. Pat. No. 5,422,121 (Röhm GmbH) discloses an oral dosage form having a core containing at least one active ingredient enclosed within a shell material which comprises a polysaccharide that decomposes in the colon in admixture with a film-forming polymer. The ratio by weight of polysaccharide to film forming polymer is from 1:2 to 5:1, preferably from 1:1 to 4:1. Premature diffusion of the active ingredient from the core can be suppressed using a gastric resistant isolating layer. The reference exemplifies inter alia tablets having an inner isolating layer of Eudragit® L30D with an outer layer comprising Eudragit® L30D and guar gum (Example 2).

WO96/36321A discloses an oral dosage form comprising a core containing bisacodyl, and an enteric polymer coating for the core, the coating comprising at least one inner coating layer and an outer coating layer. The or each the inner coating layer is an enteric polymer that begins to dissolve in an aqueous medium at a pH from about 5 to about 6.3, and the outer coating layer is an enteric polymer that begins to dissolve in an aqueous medium at a pH from about 6.8 to about 7.2. The enteric polymer coating materials for the inner layer(s) are selected from the group consisting of cellulose acetate phthalate; cellulose acetate trimellitate; hydroxypropyl methylcellulose phthalate; hydroxypropyl methylcellulose acetate succinate; polyvinyl acetate phthalate; poly(methacrylic acid, methyl methacrylate) 1:1; poly(methacrylic acid, ethyl acrylate) 1:1; and compatible mixtures thereof.

WO2007/122374A discloses a colonic drug delivery formulation in which a mixture of a pH dependent film forming polymeric material and a polysaccharide such as starch is used. Although it is known that this formulation shows delayed release followed by a relatively quick release of the drug, it would be preferred if the drug release was quicker in the colon.

In accordance with a first aspect of the present invention, there is provided a delayed release drug formulation for oral administration to deliver a drug to the colon of a subject, said formulation comprising a core and a coating for the core, the core comprising a drug and the coating comprising an outer layer and an inner layer, wherein the outer layer comprises a mixture of a first polymeric material which is susceptible to attack by colonic bacteria and a second polymeric material which has a pH threshold at about pH 5 or above, and wherein the inner layer comprises a third polymeric material that is soluble in intestinal fluid or gastrointestinal fluid, said third polymeric material being selected from the group consisting of a polycarboxylic acid polymer that is at least partially neutralised, and a non-ionic polymer, provided that, where said third polymeric material is a non-ionic polymer, said inner layer comprises at least one additive selected from a buffer agent and a base.

The Inventors have discovered that a coating having an inner layer comprising a polymer that is soluble in intestinal fluid or gastrointestinal fluid, e.g. a partially or fully neutralised polycarboxylic acid polymer, and an outer layer of a mixture of a first polymeric material susceptible to attack by colonic bacteria, e.g. a polysaccharide, and a second polymeric material which has a pH threshold at about pH 5 or above, e.g. a polycarboxylic acid polymer of the same type as the polymer of the inner layer but either non-neutralised or partially neutralised to a lower extent than the third polymeric material, has superior colonic-release properties over comparative coatings designed for site-specific release in the colon. In this connection, drug release from formulations according to the present invention appears to be accelerated in the colon when compared to comparative colonic release formulations. Without wishing to be bound by any particular theory, the Inventors believe that, once intestinal fluid or gastrointestinal fluid penetrates the outer layer, the inner layer begins to dissolve before the outer layer to form a fluid region between the core and the outer layer. The fluid region not only facilitates dissolution and/or disintegration of the outer layer from the inside, but also softens and begins to break up the core so that, when the outer layer degrades, the drug is released from the core more quickly.

It is preferred that the first polymeric material comprises at least one polysaccharide selected from the group consisting of starch; amylose; amylopectin; chitosan; chondroitin sulfate; cyclodextrin; dextran; pullulan; carrageenan; scleroglucan; chitin; curdulan and levan. It is particularly preferred that the first polymeric material is starch.

In preferred embodiments, the second polymeric material is an anionic polymeric material, and more preferably an anionic copolymer of a (meth)acrylic acid and a (meth)acrylic acid alkyl ester.

The third polymeric material is preferably an anionic polymeric material and more preferably an at least partially neutralised, preferably fully neutralised, copolymer of a (meth)acrylic acid and a (meth)acrylic acid alkyl ester.

In a preferred embodiment, the second polymeric material is the same type of copolymer of a (meth)acrylic acid and a (meth)acrylic acid alkyl ester as the third polymeric material prior to neutralisation.

In a particularly favourable embodiment, the present invention relates to a delayed release drug formulation comprising a core and a coating for the core, the core comprising a drug; and the coating comprising an outer layer and an inner layer, wherein the outer layer comprises a mixture of starch and a copolymer of a (meth)acrylic acid and a (meth)acrylic acid $C_{1-4}$ alkyl ester; and the inner layer comprises a fully neutralized copolymer of a (meth)acrylic acid and a (meth)acrylic acid $C_{1-4}$ alkyl ester.

Some materials that are susceptible to attack by colonic bacteria, e.g. amylose, swell when exposed to aqueous fluid, e.g. gastrointestinal fluid. Such swelling is undesirable since it results typically in premature release of the drug. The swelling is controlled by the inclusion of a pH dependent material having a pH threshold of pH 5 or above.

A further technical advantage of the present invention (compared, for example, to the formulation disclosed in WO01/76562A) is that substantially no drug is released for an extended period (that is, whilst the coating is intact and is being dissolved/disintegrated), following which the drug is released relatively quickly. This is in contrast to homogeneous tablets from which the drug release profile is gradual from the outset rather than delayed then pulsatile.

A yet further technical advantage of the present invention compared to WO2007/122374A is accelerated release of the drug once the formulation is exposed to the conditions of the colonic environment.

First Polymeric Material

The first polymeric material typically comprises a polysaccharide, preferably containing a plurality of glucose units, e.g. a polyglucoside. In a preferred embodiment, the polysaccharide is at least one polysaccharide selected from the group consisting of starch; amylose; amylopectin; chitosan; chondroitin sulfate; cyclodextrin; dextran; pullulan; carrageenan; scleroglucan; chitin; curdulan and levan. It is further preferred that the polysaccharide is starch, amylose or amylopectin, most preferably starch.

The person skilled in the art is capable of determining whether a polymeric material is susceptible to attack by colonic bacteria using techniques comprising part of the common general knowledge. For example, a pre-determined amount of a given material could be exposed to an assay containing an enzyme from a bacterium found in the colon and the change in weight of the material over time may be measured.

The polysaccharide is preferably starch. Starches are usually extracted from natural sources such as cereals; pulses; and tubers. Suitable starches for use in the present invention are typically food grade starches and include rice starch; wheat starch; corn (or maize) starch; pea starch; potato starch; sweet potato starch; tapioca starch; sorghum starch; sago starch; and arrow root starch. The use of maize starch is exemplified below.

Starch is typically a mixture of two different polysaccharides, namely amylose and amylopectin. Different starches may have different proportions of these two polysaccharides. Most natural (unmodified) maize starches have from about 20 wt % to about 30 wt % amylose with the remainder being at least substantially made up of amylopectin. Starches suitable for use in the present invention typically have at least 0.1 wt %, e.g. at least 10% or 15%, preferably at least 35 wt %, amylose.

"High amylose" starches, i.e. starches having at least 50 wt % amylose, are suitable. Particularly suitable starches have from about 55 wt % to about 75 wt %, e.g. about 60 wt % or about 70 wt % amylose. In particular, starches having from about 50 wt % to about 60 wt % amylose are also suitable, Starches suitable for use in the present invention may have up to 100% amylopectin, more typically from about 0.1 wt % to about 99.9 wt % amylopectin. "Low amylose" starches, i.e. starches having no more than 50 wt % amylose and at least 50 wt % amylopectin, e.g. up to 75 wt % amylopectin and even as much as up to 99 wt % amylopectin, are still suitable. The starch may be, for example, unmodified waxy corn starch. This typically comprises about 100% amylopectin.

Preferred starches have no more than 50 wt % amylopectin. As indicated above, particularly suitable starches are "high amylose" starches which have from about 25 wt % to about 45 wt % amylopectin, e.g. about 30 wt % or about 40 wt % amylopectin. In particular, starches having from about 40 wt % to about 50 wt % amylopectin are also suitable.

The person skilled in the art is capable of determining the relative proportions of amylose and amylopectin in any given starch. For example, near-infrared ("NIR") spectroscopy could be used to determine the amylose and amylopectin content of a starch using calibration curves obtained by NIR using laboratory-produced mixtures of known amounts of these two components. Further, starch could be hydrolysed to glucose using amyloglucosidase. A series of phosphorylation and oxidation reactions catalysed by enzymes result in the formation of reduced nicotinamide adenine dinucleotide phosphate ("NADPH"). The quantity of NADPH formed is stoichiometric with the original glucose content. Suitable test kits for this procedure are available (e.g., R-Biopharm GmbH, Germany). Another method that could be used involves subjecting the coating to digestion by bacterial enzymes, e.g. α-amylase, to produce short chain fatty acids ("SCFA") which can be quantified by gas-liquid chromatography using a capillary column.

Preferred starches have amylose in its glassy form although amylose in its amorphous form may also be used in conjunction with the present invention.

Preferred starches are "off-the-shelf" starches, i.e. starches which require no processing prior to use in the context of the present invention. Examples of particularly suitable "high amylose" starches include Hylon™ VII (National Starch, Germany), Eurylon™ 6 (or VI) or Amylo NI-460 or Amylo N-400 (Roquette, Lestrem, France), or Amylogel 03003 (Cargill, Minneapolis, USA) all of which are examples of a maize starch having from about 50 wt % to about 75 wt % amylose.

Second Polymeric Material

The present invention involves the use of a second polymeric material that dissolves in a pH dependent manner. The second material is a film forming polymer that is pH sensitive, i.e. has a "pH threshold" which is the pH below which it is insoluble in aqueous media and at or above which it is soluble in aqueous media. Thus, the pH of the surrounding medium triggers dissolution of the second polymeric material and none (or essentially none) of the second polymeric material dissolves below the pH threshold. Once the pH of the surrounding medium reaches (or exceeds) the pH threshold, the second polymeric material becomes soluble.

Throughout the specification, the term "insoluble" is used to mean that 1 g of a polymeric material requires more than 10,000 ml of solvent or "surrounding medium" to dissolve at a given pH. In addition, the term "soluble" is used to mean that 1 g of a polymeric material requires less than 10,000 ml, preferably less than 5,000 ml, more preferably less than 1000 ml, even more preferably less than 100 ml or 10 ml of solvent or surrounding medium to dissolve at a given pH.

By "surrounding medium", the Inventors mean gastric fluid and intestinal fluid, or an aqueous solution designed to recreate in vitro gastric fluid or intestinal fluid.

The normal pH of gastric juice is usually in the range of pH 1 to 3. The second polymeric material is insoluble below pH 5 and soluble at about pH 5 or above and, thus, is usually insoluble in gastric juice. Such a material may be referred to as a gastro-resistant material or an "enteric" material.

The second polymeric material has a pH threshold of pH 5 or above, e.g. about pH 5.5 or above, preferably about pH 6 or above and more preferably about pH 6.5 or above. The second polymeric material typically has a pH threshold of no more than about pH 8, e.g. no more than about pH 7.5 and preferably no more than about pH 7.2. Preferably, the second polymeric material has a pH threshold within the range of pH found in intestinal fluid. The pH of intestinal fluid may vary from one person to the next, but in healthy humans is generally from about pH 5 to 6 in the duodenum, from about 6 to 8 in the jejunum, from about 7 to 8 in the ileum, and from about 6 to 8 in the colon. The second polymeric material preferably has a pH threshold of about 6.5, i.e. is insoluble below pH 6.5 and soluble at about pH 6.5 or above, and more preferably has a pH threshold of about 7, i.e. is insoluble below pH 7 and soluble at about pH 7 or above.

The pH threshold at which a material becomes soluble may be determined by a simple titration technique which would be part of the common general knowledge to the person skilled in the art.

The second polymeric material is typically a film-forming polymeric material such as a polymethacrylate polymer, a cellulose polymer or a polyvinyl-based polymer. Examples of suitable cellulose polymers include cellulose acetate phthalate (CAP); cellulose acetate trimellitate (CAT); and hydroxypropylmethylcellulose acetate succinate (HPMC-AS). Examples of suitable polyvinyl-based polymers include polyvinyl acetate phthalate (PVAP).

The second material is preferably an "anionic" polymeric material, i.e. a polymeric material containing groups that are ionisable in aqueous media to form anions (see below), and more preferably a co-polymer of a (meth)acrylic acid and a (meth)acrylic acid $C_{1-4}$ alkyl ester, for example, a copolymer of methacrylic acid and methacrylic acid methyl ester. Such a polymer is known as a poly(methacrylic acid/methyl methacrylate) co-polymer. Suitable examples of such co-polymers are usually anionic and not sustained release polymethacrylates. The ratio of carboxylic acid groups to methyl ester groups (the "acid:ester ratio") in these co-polymers determines the pH at which the co-polymer is soluble. The acid:ester ratio may be from about 2:1 to about 1:3, e.g. about 1:1 or, preferably, about 1:2. The molecular weight ("MW") of preferred anionic co-polymers is usually from about 120,000 to 150,000 g/mol, preferably about 125,000 g/mol or about 135,000 g/mol.

Preferred anionic poly(methacrylic acid/methyl methacrylate) co-polymers have a molecular weight of about 125,000 g/mol. Suitable examples of such polymers have an acid:ester ratio of about 1:1 and a pH threshold of about pH 6, or have an acid:ester ratio of about 1:2 and a pH threshold of about pH 7.

A specific example of a suitable anionic poly(methacrylic acid/methyl methacrylate) co-polymer having a molecular weight of about 125,000 g/mol, an acid:ester ratio of about 1:1 and a pH threshold of about pH 6 is sold under the trade mark Eudragit® L. This polymer is available in the form of a powder (Eudragit® L 100), or as an organic solution (12.5%) (Eudragit® L 12.5).

A specific example of a suitable anionic poly(methacrylic acid/methyl methacrylate) co-polymer having a molecular weight of about 125,000 g/mol, an acid:ester ratio of about 1:2 and a pH threshold of about pH 7 is sold under the trade mark Eudragit® S. This polymer is available in the form of a powder (Eudragit® S 100) or as an organic solution (12.5%) (Eudragit® S 12.5).

The second polymeric material may be a co-polymer of methacrylic acid and ethyl acrylate. Preferred poly(methacrylic acid/ethyl acrylate) co-polymers have a molecular weight from about 300,000 to 350,000 g/mol, e.g. about 320,000 g/mol. Suitable examples of such co-polymers have an acid:ester ratio of about 1:1 and a pH threshold of about pH 5.5.

A specific example of a suitable anionic poly(methacrylic acid/ethyl acrylate) co-polymer is available in the form of a powder and sold under the trade mark Eudragit® L 100-55, or in the form of an aqueous dispersion (30%) and sold under the trade mark Eudragit® L 30 D-55.

The second polymeric material may be a co-polymer of methyl acrylate, methyl methacrylate and methacrylic acid. Preferred poly(methyl acrylate/methyl methacrylate/methacrylic acid) co-polymers have a molecular weight from about 250,000 to about 300,000 g/mol, e.g. about 280,000 g/mol. Suitable examples of such co-polymers have a methyl acrylate:methyl methacrylate:methacrylic acid ratio of about 7:3:1 thereby providing an acid:ester ratio of about 1:10 and a pH threshold of about pH 7.

A specific example of a suitable anionic poly(methyl acrylate/methyl methacrylate/ethyl acrylate) co-polymer is available in the form of an aqueous dispersion (30%) and is sold under the trade mark Eudragit® FS 30 D.

The Eudragit® co-polymers are manufactured and/or distributed by Evonik GmbH, Darmstadt, Germany.

Mixtures of film forming polymer materials may be used as appropriate. For example, the second polymeric material may be a blend of at least two different polymers having a pH threshold of about pH 5 and above. Preferably, the polymers in the blend are different polymethacrylate polymers. In embodiments where the second polymeric material is a blend of two different polymers having a pH threshold of about pH 5 or above, the polymers may be present in the blend in a polymer weight ratio from about 1:99 to about 99:1, .e.g. from about 10:90 to about 90:10, or from 25:75 to about 75:25, or from about 40:60 to about 60:40, for example about 50:50.

An example of a suitable mixture would include a mixture, e.g. a 1:1 mixture, of Eudragit® L and Eudragit® S. A further example would include a blend, e.g. a 50:50 blend, of Eudragit S and Eudragit FS.

For the avoidance of doubt, the terms "mixture" and "blend" in the context of mixtures or blends of polymers forming the second polymeric material, are used herein interchangeably.

However, the use of a particular film forming polymer material, e.g. a poly(methacrylic acid/methyl methacrylate) co-polymer, alone is preferred. The use of Eudragit® S alone as the second polymeric material is particularly preferred.

Outer Layer

The proportion of the first polymeric material to the second polymeric material is typically at least 1:99, e.g. at least 10:90 and preferably at least 25:75. The proportion is typically no more than 99:1, e.g. no more than 75:25 and preferably no more than 60:40. In some embodiments, the proportion may be no more than 35:65. In some preferred embodiments, the proportion is from 10:90 to 75:25, e.g. from 10:90 to 60:40 and preferably from 25:75 to 60:40. In some particularly preferred embodiments, the proportion is from 15:85 to 35:65, e.g. from 25:75 to 35:65 and preferably about 30:70. In other particularly preferred embodiments, the proportion is from 40:60 to about 60:40, e.g. about 50:50.

The mixture of first and second polymeric materials is preferably substantially homogenous.

Optionally, conventional excipients such as those excipients selected from plasticisers for film formation (for example, triethyl citrate), anti-tack agents (such as glyceryl monostearate or GMS) and surfactants (such as polysorbate 80), may be included in amounts up to 30 wt % of the final composition of the outer coating preparation.

The thickness of the outer coating of the core is typically from about 10 μm to about 150 μm. The thickness of a specific coating will, however, depend on the composition of the coating. For example, coating thickness is directly proportional to the amount of polysaccharide in the coating. Thus, in embodiments where the coating comprises high amylose starch and Eudragit™ S at a ratio of about 30:70, the coating thickness may be from about 70 μm to about 130 μm, and preferably from about 90 μm to about 110 μm. The thickness (in μm) for a given coating composition is independent of core size.

The thickness of the outer coating is not related to the size of the core but is typically equivalent to about 2 mg/cm$^2$ to about 10 mg/cm$^2$, preferably from about 2 mg/cm$^2$ to about 8 mg/cm$^2$, and most preferably from about 4 mg/cm$^2$ to about 8 mg/cm$^2$, based on the dry weight of the total polymeric material, for cores having a diameter from about $5 \times 10^{-4}$ m to about 25 mm.

Third Polymeric Material

The formulation according to the present invention additionally has an inner layer which is positioned between the core and the outer layer. The inner layer comprises a third polymeric material which may be insoluble in gastric fluid and soluble in intestinal fluid, but preferably is soluble in both gastric fluid and intestinal fluid (referred herein as gastrointestinal fluid).

By "gastric fluid", the inventors mean the aqueous fluid in the stomach of a mammal, particularly a human. The fluid contains up to about 0.1 N hydrochloric acid and substantial quantities of potassium chloride and sodium chloride, and plays a key role in digestion by activating digestive enzymes and denaturing ingested protein. Gastric acid is produced by cells lining the stomach and other cells produce bicarbonate which acts as a buffer to prevent the gastric fluid from becoming too acidic.

By "intestinal fluid", the Inventors mean the fluid in the lumen of the intestine of a mammal, particularly a human. Intestinal fluid is a pale yellow aqueous fluid secreted from glands lining the walls of the intestine. Intestinal fluid includes fluid found in the small intestine, i.e. fluid found in the duodenum (or "duodenal fluid"), fluid found in the jejunum (or "jejunal fluid") and fluid found in the ileum (or "ileal fluid"), and fluid found in the large intestine, e.g. "colonic fluid".

The skilled person can readily determine whether a polymer is soluble in gastric fluid and/or intestinal fluid. If a polymer is soluble in water (or aqueous solution), e.g. a buffer solution) at a pH from 1 to 3, then that polymer would typically be soluble in gastric fluid. Similarly if a polymer is soluble in water (or aqueous solution, e.g. a buffer solution) at a pH from 5 to 8, then that polymer would typically be soluble in intestinal fluid. Alternatively, the compositions of gastric fluid and intestinal fluid are known and may be replicated in vitro. If a polymer is soluble in artificial gastric fluid or intestinal fluid in vitro, then it would typically be soluble in gastric fluid or intestinal fluid respectively in vivo.

Any pharmacologically acceptable water soluble film forming polymers are, in principle, suitable for use as the third polymeric material. The solubility of the water soluble polymers may be dependent on pH, i.e. the third polymeric material may be a pH sensitive polymer having a pH threshold. In such embodiments, the pH threshold of the third polymeric material is less than, typically at least 0.5 pH units less than and preferably from 0.5 to 3.5 pH units less than, the pH threshold of the second polymeric material. The pH threshold of the third polymeric material is typically from about pH 4.5 to about pH 7.5.

The third polymeric material may be soluble in at least one fluid selected from gastric fluid, duodenal fluid, jejunal fluid and ileal fluid. However, in preferred embodiments, the solubility of the third polymeric material in water is not dependent on pH; at least not within the range of pH found in the intestine. In preferred embodiments, the third polymeric material is soluble in fluid at any point in the stomach and intestine, i.e. in gastrointestinal fluid.

Suitable polymers for use as the third polymeric material preferably contain groups that are ionisable in aqueous media to form anions. Such polymers are known in the art as "anionic" polymers. Suitable anionic polymers include polycarboxylic acid polymers, i.e. polymers or co-polymers that contain a plurality of carboxylic acid functional groups that are ionisable in aqueous media such as intestinal fluid, to form carboxylate anions.

In embodiments in which the third polymeric material is a polycarboxylic acid polymer, it is preferred that the third polymeric material is at least partially neutralised, i.e. that at least a portion, e.g. at least 10%, preferably at least 25%, more preferably at least 50%, and most preferably at least 90%, of the carboxylic acid groups in are the form of carboxylate anions. In particularly preferred embodiments, all of the carboxylic acid groups in the third polymeric material are in the form of carboxylate anions. Such polymers are referred to herein as "fully neutralised".

In preferred embodiments, the second and third polymeric materials are based on the same polycarboxylic acid polymer with the third polymeric material having a higher degree of neutralisation than the second polymeric material. For example, for a particular polycarboxylic acid polymer, the second polymeric material may be in non-neutralised form with the third polymeric material in partially or fully neutralised form. Alternatively, the second polymeric material may be in partially neutralised form, with the third polymeric material also in partially neutralised form (although partially neutralised to a greater extent), or in fully neutralised form.

Examples of suitable polycarboxylic acid polymers include cellulose acetate phthalate (CAP), polyvinyl acetate phthalate (PVAP), hydroxypropyl methylcellulose phthalate (HPMCP), hydroxypropyl methylcellulose acetate succinate (HPMC-AS), cellulose acetate trimellitate (CAT), xanthan gum, alginates and shellac. However, the polycarboxylic acid polymer is preferably selected from co-polymers of a (meth)acrylic acid and a (meth)acrylic acid alkyl, e.g. $C_{1-4}$ alkyl, ester and a copolymer of methacrylic acid and methacrylic acid methyl ester is particularly suitable. Such a polymer is known as a poly(methacrylic acid/methyl methacrylate) co-polymer or a "polymethacrylate". The ratio of carboxylic acid groups to methyl ester groups (the "acid:ester ratio") in these co-polymers determines the pH at which the co-polymer is soluble. The acid:ester ratio may be from about 2:1 to about 1:3, e.g. about 1:1 or, preferably, about 1:2. The molecular weight ("MW") of preferred anionic co-polymers is usually from about 120,000 to 150,000, preferably about 125,000 or about 135,000.

Preferred co-polymers for the third polymeric material are discussed in detail in the section above relating to the second polymeric material, and include Eudragit® L; Eudragit® S; Eudragit® FS 30 D; Eudragit® L30D-55; and Eudragit® L100-55.

The exemplary polymers may be used as the third polymeric material in non-neutralised form (provided the pH threshold of the polymer is less than the pH threshold of the second polymeric material—see above) or may be used in at least partially, more preferably fully, neutralised form.

Partially neutralised polymers suitable for use as the third polymeric material, and their methods of production, are known in the art, for example from US2008/0200482A and WO2008/135090A. These polymers may be fully neutralised by the addition of further base to the coating solutions.

In preferred embodiments, the third polymeric material is an at least partially, preferably fully, neutralised co-polymer of (meth)acrylic acid and a (meth)acrylic acid $C_{1-4}$ alkyl ester. In particularly preferred embodiments, the third polymeric material is a fully neutralised co-polymer of (meth)acrylic acid and (meth)acrylic acid methyl ester, particularly Eudragit® S.

The Inventors have observed that fully neutralised Eudragit® S is capable of forming a film and is readily and completely soluble in water independently of at least the range of pH found in the intestine, e.g. about pH 5 to about pH 8. Fully neutralised Eudragit® S is particularly preferred for use as the third polymeric material in the present invention.

Other polymers suitable for use as the third polymeric material include pharmacologically acceptable non-ionic polymers, i.e. pharmacologically acceptable polymers which do not ionise in aqueous media. In these embodiments, the inner layer additionally comprises at least one additive selected from a buffer agent and a base. In particular, the inner layer of these embodiments preferably comprises a base and, optionally, a buffer agent. In preferred embodiments, the inner layer comprises both a buffer agent and a base. Suitable examples of buffer agents and bases are discussed below.

Examples of suitable non-ionic polymers include methylcellulose (MC), hydroxypropyl cellulose (HPC), hydroxypropyl methylcellulose (HPMC), poly(ethyleneoxide)-graft-polyvinylalcohol, polyvinylpyrrolidinone (PVP), polyethylene glycol (PEG) and polyvinylalcohol (PVA).

Mixtures of film forming polymer materials may be used as appropriate. The polymer components in such mixtures may be anionic polymers, non-ionic polymers, or a mixture of anionic and non-ionic polymers. An example of a suitable mixture would include a mixture, e.g. a 1:1 mixture, of Eudragit® L and Eudragit® S, and a mixture, e.g. a 1:1 mixture, of Eudragit® S and HPMC. However, the use of a particular film forming polymeric material alone, e.g. a poly(methacrylic acid/methyl methacrylate) co-polymer and Eudragit® S in particular, is preferred.

Base

In preferred embodiments, the inner layer comprises at least one base. The purpose of the base is to provide an alkaline environment on the underside of the outer layer once intestinal fluid begins to penetrate the outer layer. Without being bound by any particular theory, the Inventors believe that the alkaline environment facilitates dissolution and thereby also disintegration of the outer layer since the pH of the alkaline environment is above the pH threshold of the second polymeric material, thereby accelerating release of the drug from the formulation once the outer coating is dissolved and/or disintegrates.

In principle, any pharmacologically acceptable base may be used. The base is typically a non-polymeric compound. Suitable bases include inorganic bases such as sodium hydroxide, potassium hydroxide and ammonium hydroxide, and organic bases such as triethanolamine, sodium bicarbonate, potassium carbonate, trisodium phosphate, trisodium citrate or physiologically tolerated amines such as triethylamine. Hydroxide bases in general, and sodium hydroxide in particular, are preferred.

In embodiments in which the third polymeric material is a fully neutralised polycarboxylic acid polymer, the base entrapped within the inner layer is usually the base that was used to neutralise the polymer and to adjust the pH of the inner coating preparation to a pH from about pH 7.5 to about pH 10 (see below).

In embodiments in which the third polymeric material is a non-ionic polymer, the inner layer usually comprises either a base, or more typically a combination of a base and a buffer agent.

The amount of base present in the inner layer would depend at least in part on the final pH of the inner coating preparation prior to coating a given batch of cores; the number of cores to be coated in the batch; the amount of the inner coating preparation used in the coating process of the batch; and the efficiency of the coating process in terms of the amount of wasted coating preparation.

Buffer Agent

The inner coating preferably comprises at least one buffer agent. The purpose of the buffer agent is to provide or increase pH buffer capacity on the underside of the outer layer once intestinal fluid begins to penetrate the outer layer. Without wishing to be bound by any particular theory, the Inventors believe that the buffer agent increases the buffer capacity in the dissolving inner layer and assists the ionisation and dissolution of the polymer in the outer layer. It is believed that, for a given pH, the higher the buffer capacity, the faster the rate of polymer dissolution. In embodiments where there is a base in the inner layer, the buffer agent helps maintains the alkaline environment under the outer layer once intestinal fluid penetrates the outer layer.

The buffer agent may be an organic acid such as a pharmacologically acceptable non-polymeric carboxylic acid, e.g. a carboxylic acid having from 1 to 16, preferably 1 to 3, carbon atoms. Suitable carboxylic acids are disclosed in WO2008/135090A. Citric acid is an example of such a carboxylic acid. The carboxylic acids may be used in carboxylate salt form, and mixtures of carboxylic acids, carboxylate salts or both may also be used.

The buffer agent may also be an inorganic salt such as an alkali metal salt, an alkali earth metal salt, an ammonium salt, and a soluble metal salt. As metals for the soluble metal salts, manganese, iron, copper, zinc and molybdenum can be mentioned. Further preferred, the inorganic salt is selected from chloride, fluoride, bromide, iodide, phosphate, nitrate, nitrite, sulphate and borate. Phosphates such as potassium dihydrogen phosphate are preferred over other inorganic buffer salts and organic acid buffers due to their greater buffer capacity at the pH of the coating solution, for example pH 8.

The buffer(s) is usually present in the inner layer in an amount from about 0.1 to about 20 wt %, e.g. from about 0.1 to about 4 wt %, preferably from about 0.1 to about 3 wt %, and more preferably about 1 wt %, based on the dry weight of the third polymeric material.

Inner Layer

In addition to the buffer agent and/or the base, the inner layer may comprise conventional excipients for polymer films, including those excipients selected from plasticizers (such a triethyl citrate), anti-tack agents (such as GMS), and surfactants (such as polysorbate 80).

The thickness of the inner coating of the core is typically from about 10 μm to about 150 μm. As with the outer layer, the thickness of the inner layer is not related to the size of the core but is typically equivalent to about 2 mg/cm$^2$ to about 10 mg/cm$^2$, preferably from about 2 mg/cm$^2$ to about 8 mg/cm$^2$, and most preferably from about 3 mg/cm$^2$ to about 7 mg/cm$^2$, based on the dry weight of the third polymeric material, for cores having a diameter from about 0.2 mm to about 30 mm.

Optional Additional Layers

The formulation of the present invention may have an additional (or isolation) layer either between the active core and the inner layer and/or a top coating layer coating the outer layer.

There may be formulations according to the present invention in which the composition of the core is incompatible with the delayed release coating. In such cases, it may be desirable to include an isolation layer to separate the core from the coating. For example, the present invention embraces embodiments in which the inner layer provides an alkaline environment which is thought to assist in the dissolution and degradation of the outer layer. However, if the core contains a drug having acidic groups, then the inner layer may be incompatible with the core. An example of a drug having an acidic group would be 5ASA. In such cases, it would typically be appropriate to include an isolation layer.

Any suitable isolation layer known to the skilled person can be used. In one preferred embodiment, the isolation layer comprises a non-ionic polymer. Suitable non-ionic polymers include methylcellulose (MC); hydroxypropyl cellulose (HPC); hydroxypropyl methylcellulose (HPMC); poly(ethyleneoxide)-graft-polyvinylalcohol; polyvinylpyrrolidone (PVP); polyethylene glycol (PEG); and polyvinylalcohol (PVA). Mixtures of non-ionic polymers may also be used. HPMC or PVA is preferred. The isolation layer can additionally comprise polyethylene glycol.

The formulation may also comprise an intermediate layer between the outer and inner layers, provided that the intermediate layer does not affect adversely the release characteristics of the formulation. However, the outer layer is usually provided in contact with the inner layer, that is to say the outer layer is usually applied directly on to the inner layer, i.e. there is usually no intermediate layer separating the inner and outer layers.

The Core

The "core" is the solid body on which the inner layer is applied. The core may be any suitable dosage form, for example, a tablet, a pellet, a granule, a microparticle, a hard or soft capsule, or a microcapsule. In preferred embodiments, the core is a tablet or a capsule.

The core comprises the drug(s). The drug(s) may be contained within the body of the core, for example within the matrix of a tablet or pellet, or within the contents encapsulated within a capsule. Alternatively, the drug may be in a coating applied to the core, for example where the core is a bead of edible material such as sugar, e.g. where the core is in the form of a nonpareil bead or dragée.

The core may consist of the drug(s) alone, or more usually may consist of the drug(s) and at least one pharmacologically acceptable excipient. In this connection, the core is typically a tablet or pellet and consists of a mixture of the drug(s) with a filler or diluent material, e.g. lactose or cellulose material such as microcrystalline cellulose; a binder, e.g. polyvinylpyrrolidone ("PVP") or hydroxypropyl methylcellulose (HPMC); a disintegrant, e.g. croscarmellose sodium (e.g. Ac-Di-Sol™) and sodium starch glycolate (e.g. Explotab™); and/or a lubricant, e.g. magnesium stearate and talc. The core may be a compressed granulate comprising at least some of these materials.

The core may be uncoated or, as indicated above, the core may itself comprise a coating such as an isolation layer on to which the inner layer is applied.

The minimum diameter of each core is typically at least about $10^{-4}$ m, usually at least about $5 \times 10^{-4}$ m and, preferably, at least about $10^{-3}$ m. The maximum diameter is usually no more than 30 mm, typically no more than 25 mm and, preferably, no more than 20 mm. In preferred embodiments, the core has a diameter from about 0.2 mm to about 25 mm, and preferably from about 0.2 mm to about 4 mm (e.g. for pellets or mini-tablets) or from about 15 mm to about 25 mm (e.g. for certain tablets or capsules). The term "diameter" refers to the largest linear dimension through the core.

The formulation may comprise a plurality of coated cores in order to provide a single dose of the drug(s), particularly in embodiments in which the core is "small", e.g. having a diameter of less than 5 mm. Multiunit dosage forms comprising coated cores having a diameter of less than 3 mm may be preferred.

The present invention has application in a multi-phasic drug release formulation comprising at least two pluralities of coated cores, e.g. coated pellets, in the same dosage form, e.g. a capsule, in which the coated cores of one plurality are differentiated from the coated cores of the or each other plurality by the coating. The coatings may differ from one plurality to the next in terms of coating thickness or composition, e.g. the ratio and/or identity of components. Multiphasic drug release formulations would be particularly suitable for suffers of Crohn's disease affecting different regions along the intestine.

Release from formulations according to the present invention is typically delayed until at least the distal ileum and, preferably, the colon. Release from certain formulations may also be sustained. However, in preferred formulations, release is pulsatile.

The time between initial exposure to conditions suitable for drug release and the start of drug release is known as the "lag time". The lag time depends on a number of factors including coating thickness and composition and may vary from one patient to the next. Formulations according to the present invention usually display a lag time in colonic conditions of at least 10 minutes. In most embodiments, the lag time is from about 10 minutes to about 8 hours. For example, the lag time in faecal slurry at pH 6.8 may be from about 10 minutes to about 2 hours, e.g. from about 30 minutes to about 1.5 hours. Complete release of the drug may be achieved in no more than 5 hours, e.g. no more than 4 hours, after exposure to these conditions.

A formulation is usually defined as gastric resistant if there is less than 10 wt % drug release in acidic media after 2 hours. Formulations according to the present invention typically display far less than 10 wt % drug release in acidic media and may be considered to be gastric resistant. The formulations usually display less than 1 wt % drug release in acidic media and, typically, display substantially no drug release in acidic media. When starch is combined with an acrylate film forming material to form the outer layer of the coating for the core, typically less than 5% drug release occurs over 5 hours in conditions simulating the stomach and small intestine.

In one embodiment, the core is a tablet having a diameter of 15-25 mm. The outer layer preferably comprises a 30:70 mixture of high amylose starch, e.g. Eurylon™ VII or VI, and a polymethacrylate polymer, e.g. Eudragit™ S, and the inner layer preferably comprises a fully neutralized polymethacrylate polymer, e.g. Eudragit™ S, applied from an inner coating preparation having a pH of about 8. The core is preferably coated with the inner layer to a thickness from about 3 to about 7 mg/cm² (based on dry weight of the polymethacrylate polymer) to form an inner layer coated core, which is then coated with the outer layer to a thickness from about 4 to about 8 mg/cm² (based on dry weight of polymethacrylate polymer).

Different Aspects

According to a second aspect of the present invention, there is provided a formulation according to the first aspect for use in a method of medical treatment of the human or animal body by therapy.

The core comprises at least one drug. The formulation is usually used to administer a single drug as the sole therapeutically active component. However, more than one drug may be administered in a single formulation.

The formulation of the present invention is designed to administer a wide range of drugs. Suitable drugs include those drugs which are known for intestinal administration using known delayed release oral formulations. The present invention may be used to administer drugs having a local or a systemic effect.

The formulation of the present invention has particular application in the intestinal administration of a drug comprising at least one acidic group such as a carboxylic acid group. Such drugs may be acidic drugs or zwitterionic drugs. An example of such a drug is 5-aminosalicylic acid (5ASA or mesalazine).

The identity of the drug(s) in the formulation obviously depends on the condition to be treated. In this connection, the formulation has particular application in the treatment of IBD (including Crohn's disease and ulcerative colitis); IBS; constipation; diarrhea; infection; and carcinoma, particularly colon or colorectal cancer.

For the treatment or prevention of IBD, the formulation may comprise at least one drug selected from the group consisting of anti-inflammatory agents (e.g. 5ASA (otherwise known as mesalazine or mesalamine), 4ASA, sulphasalazine and balsalazide); non-steroidal anti-inflammatory agents (e.g. ibuprofen and diclofenac); steroids (e.g. prednisolone; budesonide or fluticasone); immunosuppressants (e.g. azathioprine; cyclosporin; and methotrexate); antibiotics; and biological agents including peptides, proteins and antibody fragments. Suitable examples of biological agents include alkaline phosphatase and anti-TNF antibodies such as infliximab, adalimumab, certulizumab pegol, golimumab and ustekinumab.

For the treatment or prevention of cancer, the formulation may comprise at least one antineoplastic agent. Suitable antineoplastic agents include fluorouracil; methotrexate; dactinomycin; bleomycin; etoposide; taxol; vincristine; doxorubicin; cisplatin; daunorubicin; VP-16; raltitrexed; oxaliplatin; and pharmacologically acceptable derivatives and salts thereof. For the prevention of colon cancer or colorectal cancer, primarily in patients suffering from colitis, the formulation may comprise the anti-inflammatory agent, 5ASA.

For the treatment or prevention of IBS, constipation, diarrhea or infection, the formulation may comprise at least one active agent suitable for the treatment or prevention of these conditions.

Pharmacologically acceptable derivatives and/or salts of the drugs may also be used in the formulation. An example of a suitable salt of prednisolone is methyl prednisolone sodium succinate. A further example is fluticasone propionate.

The present invention has particular application in either the treatment of IBD (particularly, ulcerative colitis) or the prevention of colon cancer or colorectal cancer (primarily in colitis patients), both using 5ASA. It also has application as a portal of entry of drugs into the systemic circulation via the colon. This is particularly advantageous for peptide and protein drugs which are unstable in the upper gastrointestinal tract. The present invention may also be utilised for the purpose of chronotherapy.

In a third aspect of the invention, there is provided a method of targeting a drug to the colon comprising administering to a patient a formulation as defined above.

In a fourth aspect of the invention, there is provided the use of a formulation as defined above in the manufacture of a medicament for the treatment or prevention of IBD (particularly ulcerative colitis); IBS; constipation; diarrhea; infection; and cancer.

There is also provided the use of at least one drug selected from anti-inflammatory agents and steroids in the manufacture of a medicament comprising a formulation as defined above for use in the treatment of IBD. In addition, there is also provided the use of at least one antineoplastic agent in the manufacture of a medicament comprising a formulation as defined above for use in the treatment of carcinoma. Further, there is also provided use of 5ASA in the manufacture of a medicament comprising a formulation as defined above for use in the prevention of colon cancer or colorectal cancer.

According to a fifth aspect of the present invention, there is provided a method of medical treatment or prevention of IBD or carcinoma comprises administering to a patient a therapeutic amount of a formulation as defined above.

The formulation will typically comprise a therapeutically effective amount of the or each drug which may be from about 0.01 wt % to about 99 wt %, based on the total weight of the formulation. The actual dosage would be determined by the skilled person using his common general knowledge. However, by way of example, "low" dose formulations typically comprise no more than about 20 wt % of the drug, and preferably comprise from about 1 wt % to about 10 wt %, e.g. about 5 wt %, of the drug. "High" dose formulations typically comprise at least 40 wt % of the drug, and preferably from about 45 wt % to about 85 wt %, e.g. about 50 wt % or about 80 wt %.

Method

According to a sixth aspect of the present invention, there is provided a method of producing a delayed release drug formulation for oral administration to deliver a drug to the colon according to the first aspect. The method comprises:

forming a core comprising a drug;
coating the core using an inner coating preparation comprising the third polymeric material as defined above, in a solvent system to form an inner coated core;
coating the inner coated core with an outer coating preparation comprising a first polymeric material which is susceptible to attack by colonic bacteria and a second polymeric material which has a pH threshold of about pH 5 or above in a solvent system, to form an outer coated core, wherein, where the third polymeric material is a non-ionic polymer, the inner coating preparation comprises at least one additive selected from the group consisting of a buffer agent and a base.

The solvent system of the inner coating preparation is preferably aqueous.

In embodiments where the third polymeric material is an at least partially neutralised polycarboxylic acid polymer, said method typically comprises dispersing a polycarboxylic acid polymer in a solvent, optionally with a buffer agent, and adding base to at least partially neutralise the polycarboxylic acid polymer to form the inner coating preparation. In preferred embodiments, the amount of base added is at least sufficient to fully neutralise the polycarboxylic acid polymer.

In embodiments where the third polymeric material is a non-ionic polymer, the pH of the inner coating preparation is preferably adjusted prior to coating to be at least 0.5 pH units higher than the pH threshold of the second polymeric material.

The pH of the inner coating preparation is preferably adjusted to be from about pH 7.5 to about pH 10, e.g. from about pH 7.5 to about pH 8.5, preferably from about pH 7.8 to about pH 8.2, and more preferably about pH 8.

The outer coating may be applied using the method described in WO2007/122374A.

Food Effect

The drug release profile from a conventional delayed release dosage form is often dependent on the state of the stomach, i.e. whether the stomach is in the "fed" state or the "fasted" state. In brief, the "fed state" leads to enhanced gastric residence time which can influence $t_{lag}$, i.e. the time before initial release of the drug from the dosage form. In addition, fast in vivo dissolution after leaving the stomach may lead to an increase in $C_{max}$, or the peak blood plasma concentration for the drug.

The dependency of drug release on the state of the stomach is known colloquially as the "food effect" and is the reason why conventional dosage forms are often to be administered either on an empty stomach, or with or just after food. Clearly, a significant food effect is undesirable as it dictates when an oral dosage form may be administered which could have an adverse effect on patient compliance due to premature drug release.

The fasted and fed states can be simulated in vitro by exposing dosage forms initially to either 0.1N HCl for 2 hours (fasted state) or to Fed State Simulated Gastric Fluid (FeSSGF) at pH 5 for 4 hours. After the simulated fasted or fed states, the tablets are further exposed to Hanks buffer at pH 6.8 for at least 4 hours which simulates the conditions in the small intestine. Exposing the tablets for longer than 4 hours, e.g. for 10 hours as in the examples discussed below, can provide an indication of the "robustness" of the tablets.

An example of FeSSGF is described in Jantratid et al (2008) "*Dissolution media simulating conditions in the proximal human gastrointestinal tract: An update.*" (Pharm. Res. 25(7): 1663-1676). In brief, this example of FeSSGF is composed of a mixture (50:50) of milk and acetic acid/sodium acetate buffer and sodium chloride.

By way of example, the Inventors have observed that coated 800 mg 5ASA tablets (coated with single coating of Eudragit S) demonstrate shorter $t_{lag}$ when exposed in vitro to this simulated fed state conditions compared to the simulated fasted state conditions. Earlier initial release of 5ASA may result in absorption of the drug in the small intestine which could lead to an increase in systemic side effects. A similar effect is also observed both in vitro and in vivo for Lialda®/Mezavant®, a 1200 mg 5ASA tablet formulation from Cosmo Pharmaceuticals/Shire intended for site specific colonic release of 5ASA.

The Inventors have discovered that formulations defined above according to the present invention which the outer layer is applied from "semi organic" coating preparation display similar release profiles after both fasted and fed simulated gastric conditions. The increase in $t_{lag}$ in the fed state at least reduces and possibly eliminates the undesirable food effect, which in turn leads to a reduction in the occurrence of systemic side effects and potentially an improvement in patient compliance since the dose form can be taken at any time, with or without food.

The "semi organic" coating preparation is prepared from an aqueous dispersion of the first polymeric material and an organic (typically, ethanolic) solution of the second polymeric material. Preferred first and second polymeric materials, and their relative proportions, are as defined above.

Alcohol Effects

Alcohol-induced premature release (dose dumping) has been observed for coated 5ASA dosage forms (see Fadda et al (2008) "*Impairment of drug release from modified release formulations in the presence of alcohol*" Int. J. Pharm. 360; 171-176). Preliminary results indicate that, when exposed to 40% ethanol in 0.1N HCl for 2 hours, formulations according to the present invention are more resistant to alcohol-induced degradation in the stomach and hence do not suffer significantly from an alcohol effect. Further studies are proposed to confirm the preliminary results.

EXAMPLES

Preferred embodiments of the present invention will now be described with reference to the drawings, in which:—

FIG. 1 is a graph comparing drug release as a function of time from 400 mg 5ASA tablets coated with (a) a single layer of Eudragit® S alone (Comparative Example 1), (b) a single layer of a 30:70 mixture of starch and Eudragit® S (Comparative Example 2), (c) an inner layer of fully neutralised Eudragit® S and an outer layer of Eudragit® S (Comparative Example 3), or (d) an inner layer of fully neutralised Eudragit® S and an outer layer of a 30:70 mixture of starch and Eudragit® S (Example 1), when exposed to 0.1N HCl for 2 hours and then Kreb's buffer (pH 7.4) for 8 hours;

FIG. 2 is a graph comparing drug release as a function of time from 400 mg 5ASA tablets coated with (a) a single layer of a 30:70 mixture of starch and Eudragit® S (Comparative Example 2), (b) an inner layer of fully neutralised Eudragit® S and an outer layer of Eudragit® S (Comparative Example 3), or (c) an inner layer of fully neutralised Eudragit® S and an outer layer a 30:70 mixture of starch and Eudragit® S (Example 1), when exposed to faecal slurry at pH 6.8 for 24 hours;

Figure 5:
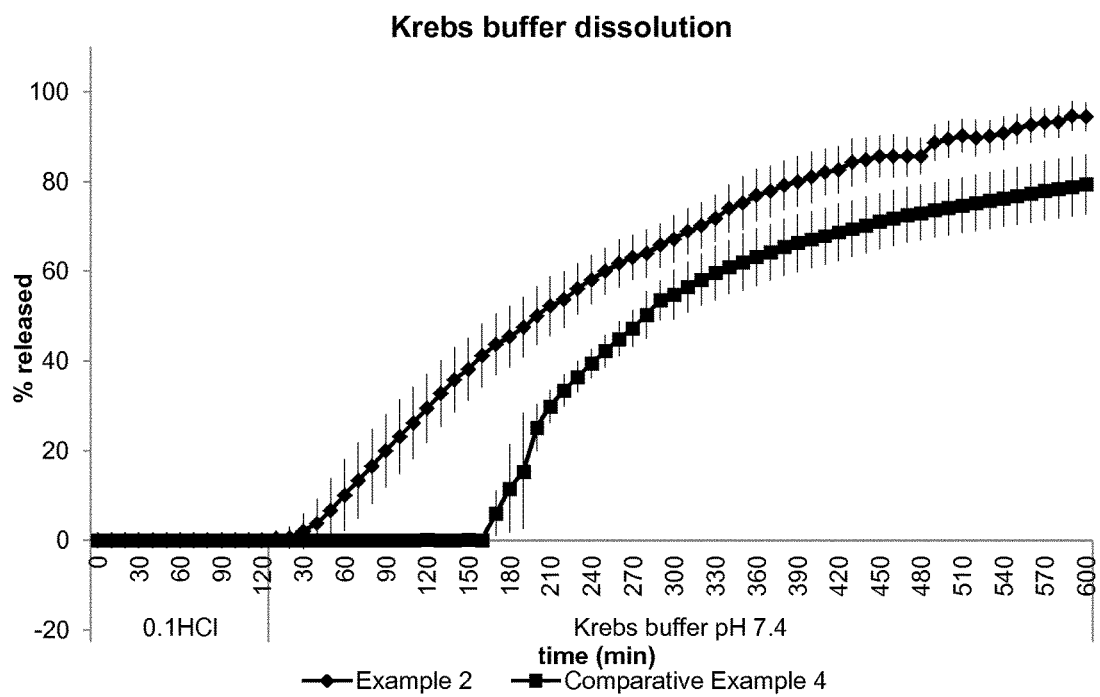
Figure 6:
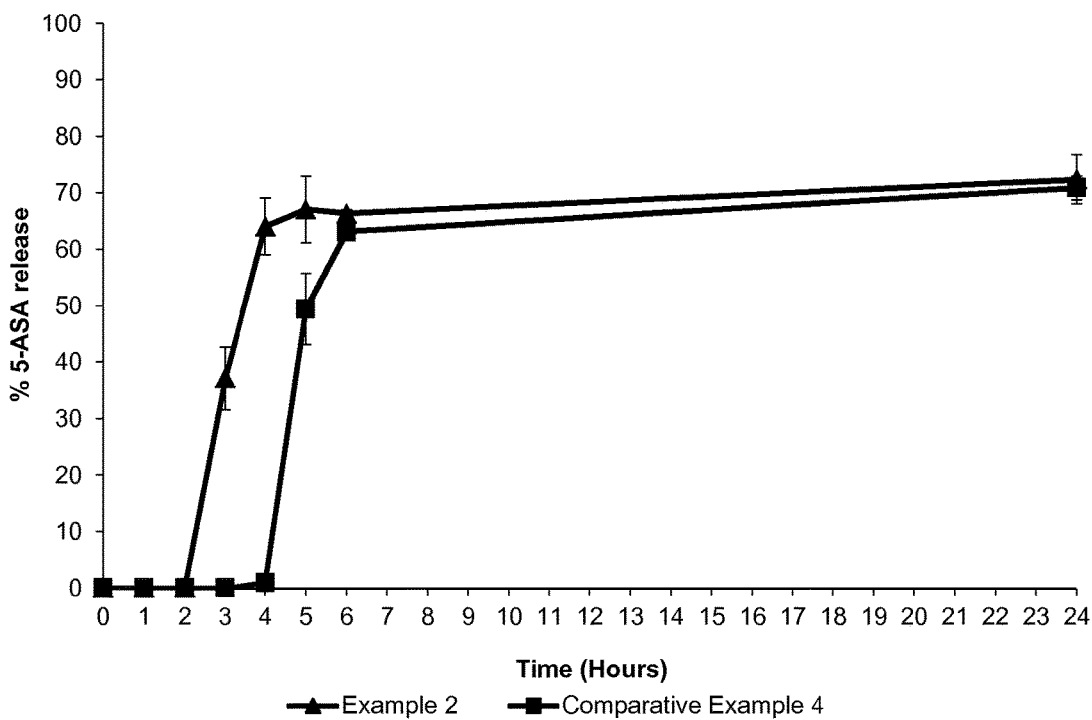
Figure 7:
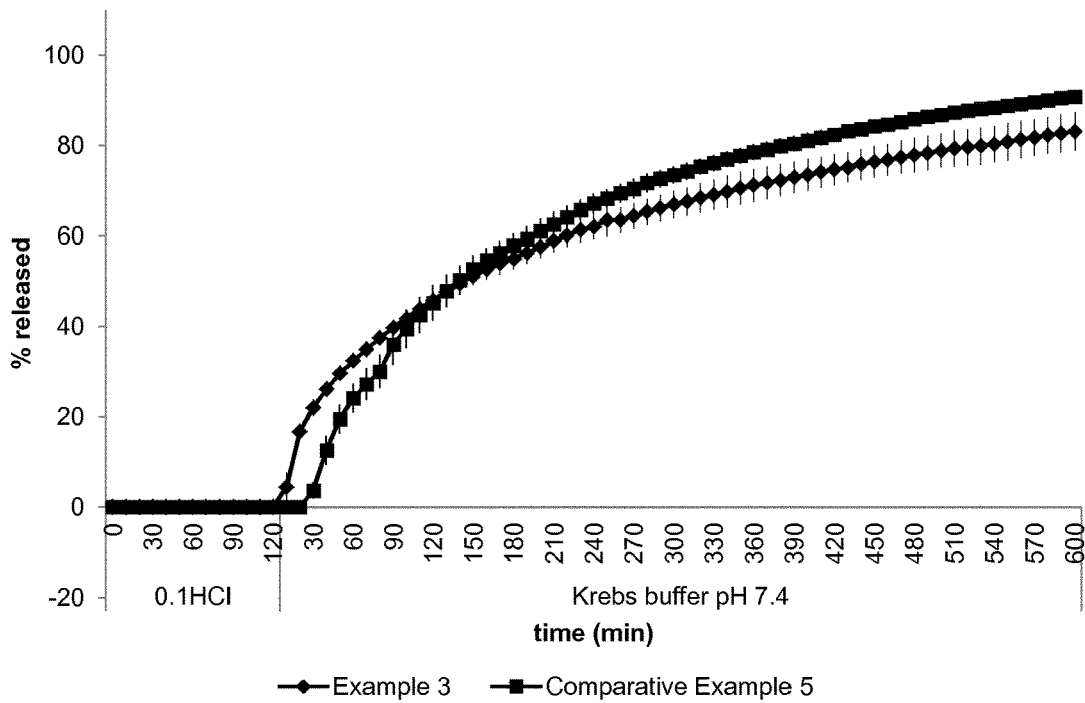
Figure 8:
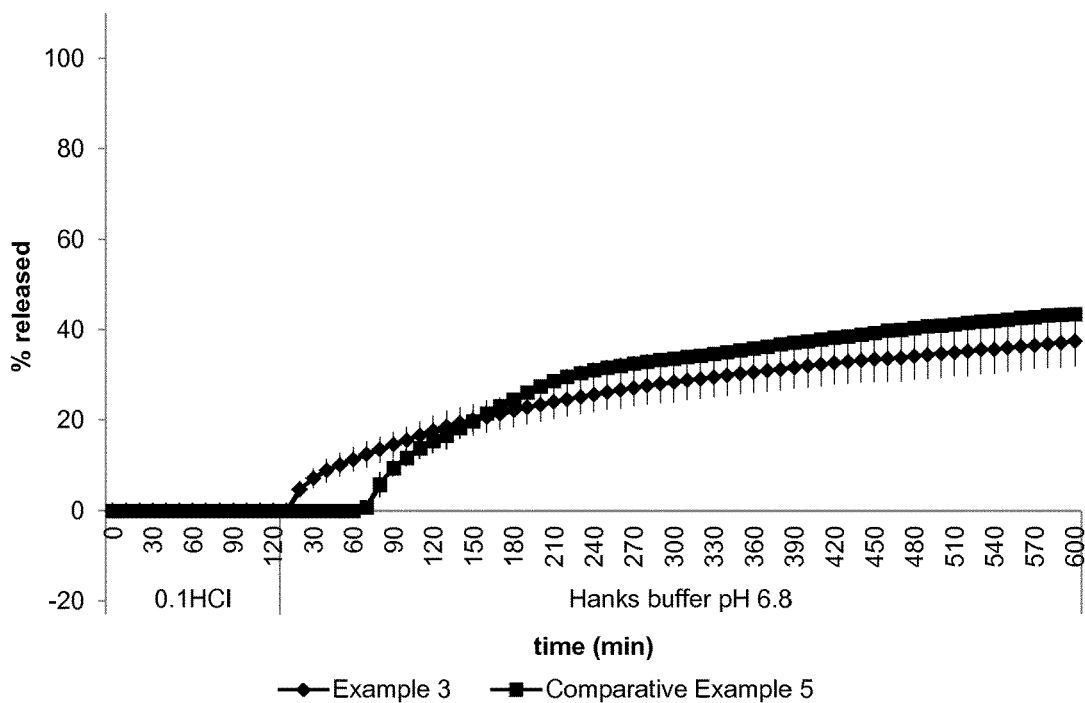
Figure 9:
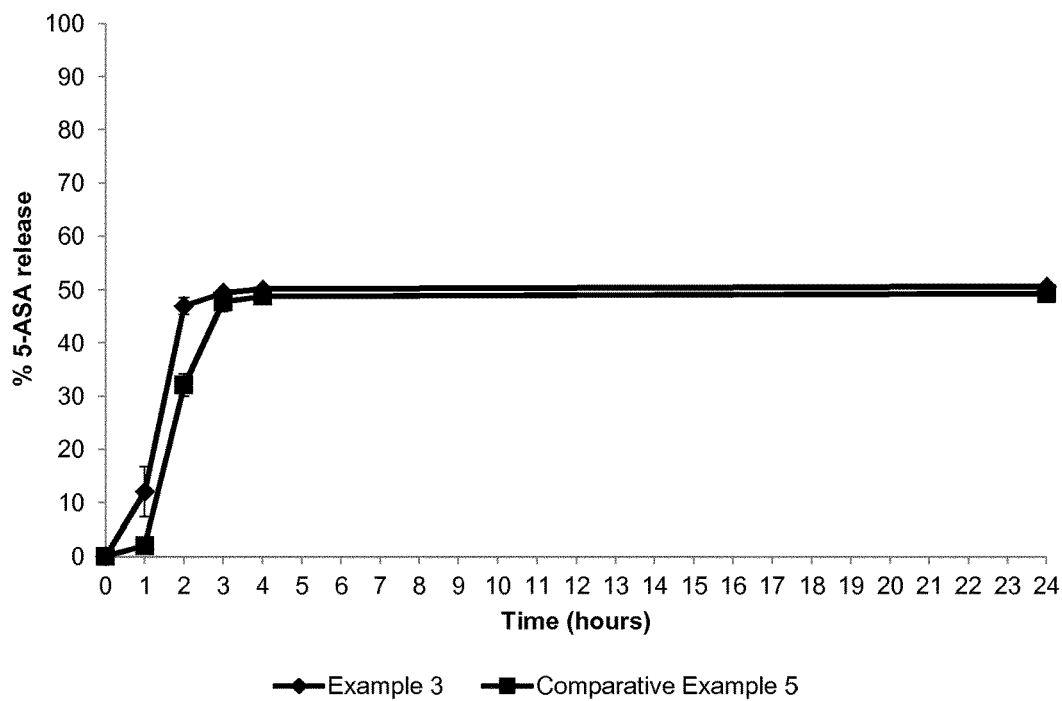
Figure 10:
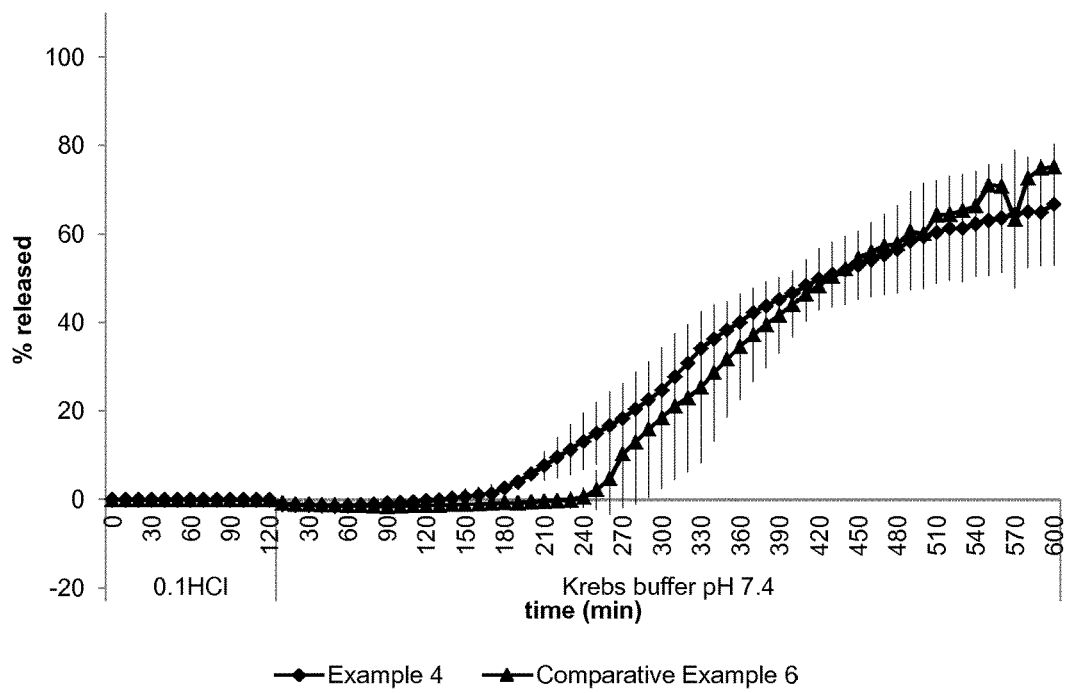
Figure 11:
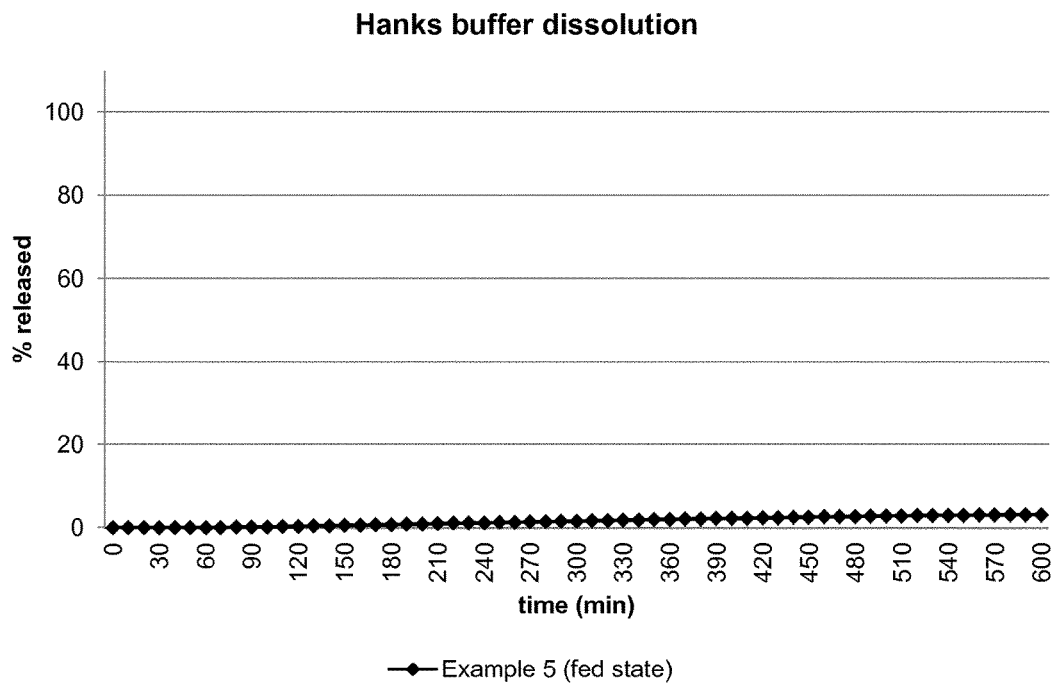
Figure 12:
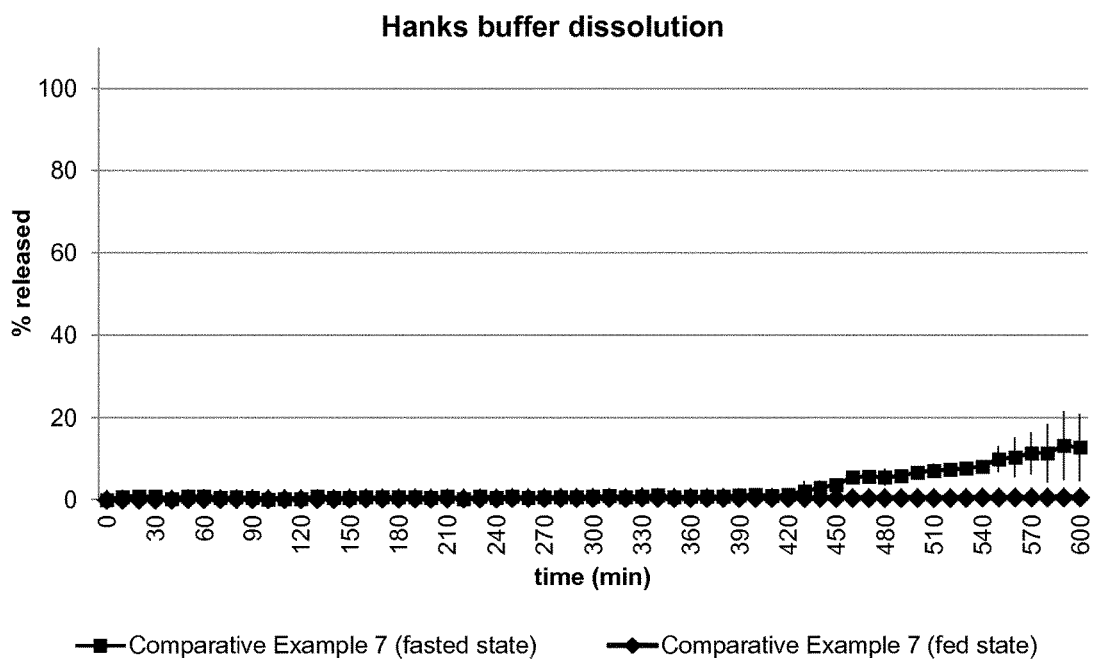
Figure 13:
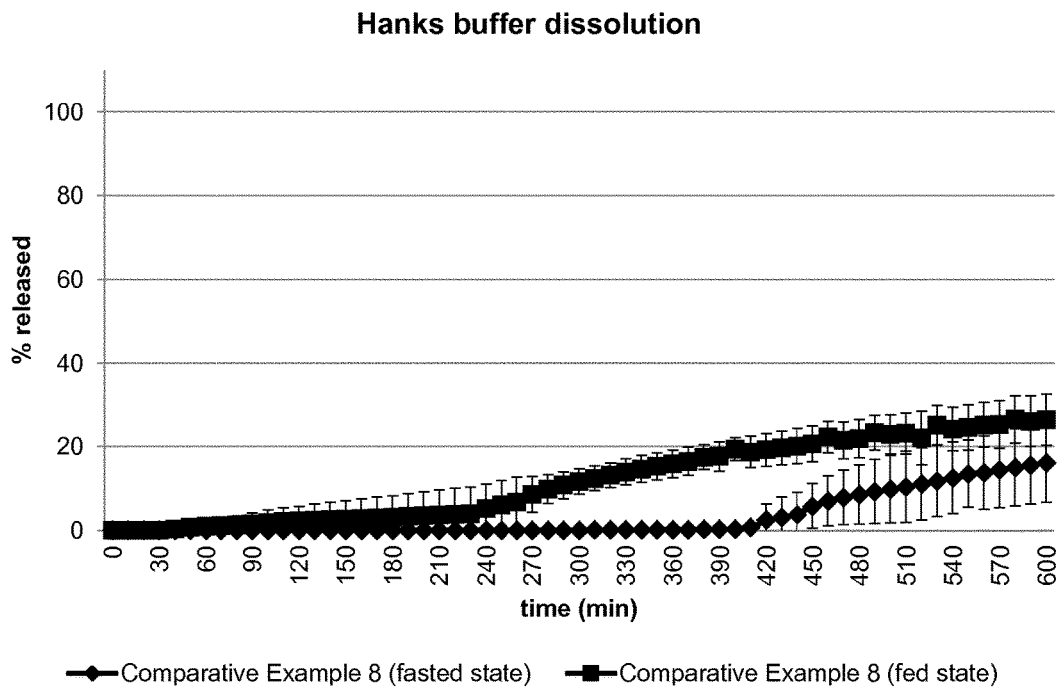
Figure 14:
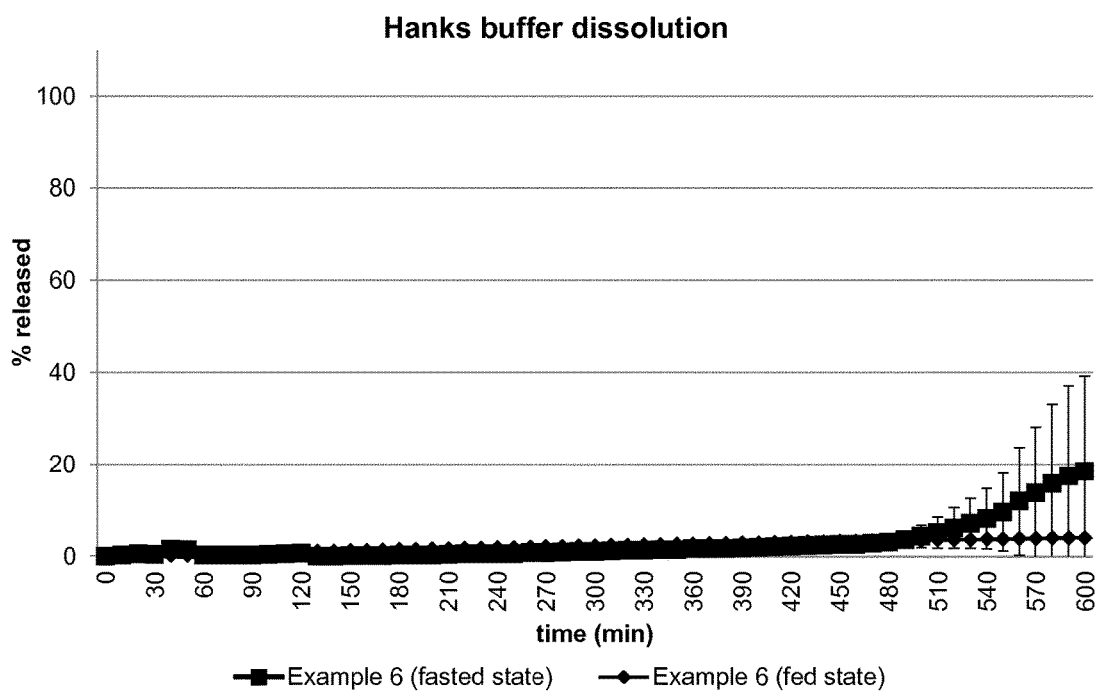
Figure 15:
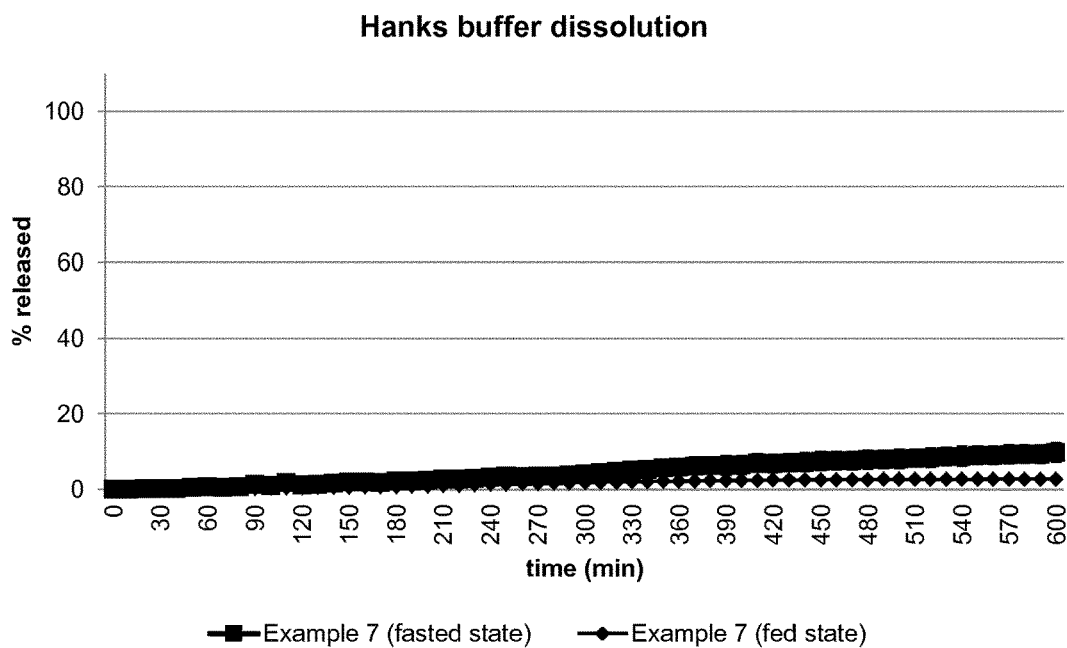
Figure 16:
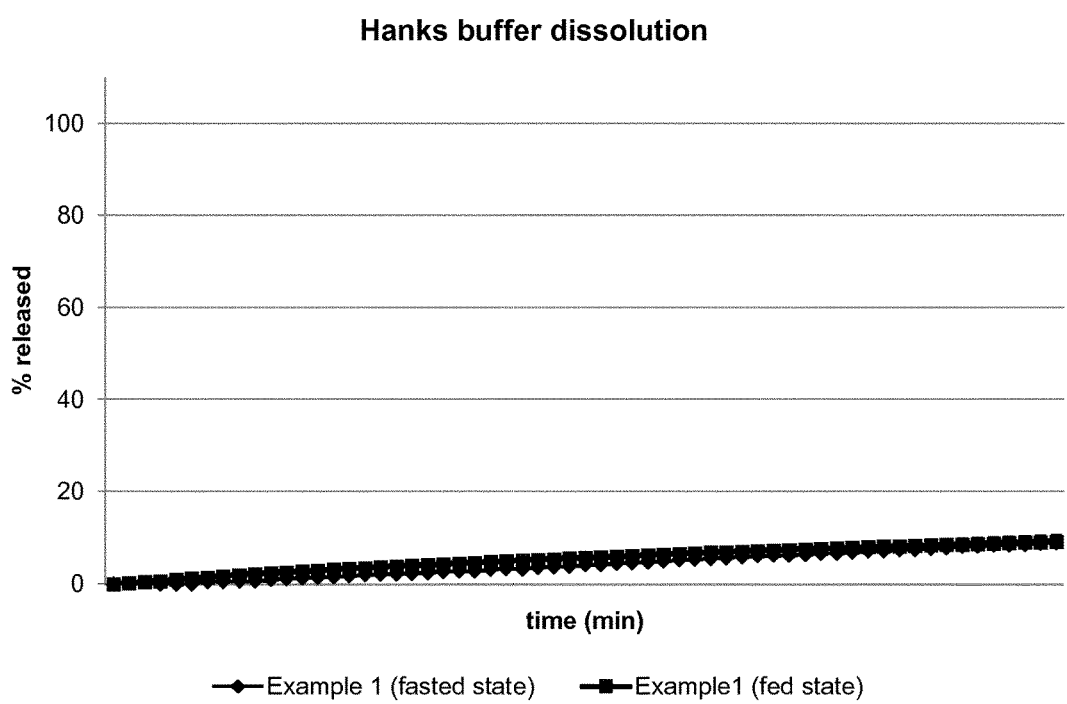

FIG. 5 is a graph comparing drug release as a function of time from 1200 mg 5ASA tablets coated with (a) an inner layer of fully neutralised Eudragit® L30D-55 and an outer layer of a 30:70 mixture of starch and Eudragit® S (Example 2) and (b) an inner layer of Eudragit® L30D-55 (not neutralised) and an outer layer of a 30:70 mixture of starch and Eudragit® S (Comparative Example 4), when exposed to 0.1N HCl for 2 hours and then Kreb's buffer (pH 7) for 10 hours;

FIG. 6 is a graph comparing drug release as a function of time from tablets of Example 2 and Comparative Example 4, when exposed to faecal slurry at pH 6.5 for 24 hours;

FIG. 7 is a graph comparing drug release as a function of time from 1200 mg 5ASA tablets coated with (a) an inner layer of neutralized Eudragit® L30D-55 and an outer layer of a 3:1 mixture of guar gum and Eudragit® L30D-55 (Example 3) and (b) an inner layer of Eudragit® L30D-55 (not-neutralized) and an outer layer of a 3:1 mixture of guar gum and Eudragit® L30D-55 (Comparative Example 5) when exposed to 0.1N HCl for 2 hours and then Krebs buffer (pH 7.4) for 10 hours;

FIG. 8 is a graph comparing drug release as a function of time from tablets of Example 3 and Comparative Example 5 when exposed to 0.1N HCl for 2 hours and then Hanks buffer (pH 6.8) for 10 hours;

FIG. 9 is a graph comparing drug release as a function of time from tablets of Example 3 and Comparative Example 5 when exposed to faecal slurry at pH 6.5 for 24 hours;

FIG. 10 is a graph comparing drug release, as a function of time from 1200 mg 5ASA tablets coated with (a) an isolation layer of polyvinyl alcohol (Opadry II 85F), an inner layer of polyvinyl alcohol (Opadry II 85F) adjusted to pH 8 and 20% buffer salt, and an outer layer of a blend of Eudragit® S/Eudragit® FS in a 70:30 mixture with starch (Example 4) and (b) an isolation layer made of polyvinyl alcohol (Opadry II 85F) and an outer layer made of a blend of Eudragit® S/Eudragit® FS in a 70:30 mixture with starch (Comparative Example 6) when exposed to 0.1N HCl for 2 hours and then Krebs buffer (pH 7.4) for 10 hours;

FIG. 11 is a graph comparing drug release as a function of time from 1200 mg 5ASA tablets coated with an isolation layer of HPMC, an inner layer of neutralized Eudragit® S and an outer layer of 30:70 starch:Eudragit® S applied from a "semi organic" coating preparation (Example 5) when exposed to FeSSGF at pH 5 for 4 hours (fed state), and then to Hanks buffer at pH 6.8 for 10 hours (only the Hanks buffer stage is presented);

FIG. 12 is a graph comparing drug release as a function of time from 1200 mg 5ASA tablets coated with an isolation layer of HPMC and an outer layer of 30:70 starch:Eudragit® S applied from a "semi organic" coating preparation (Comparative Example 7) when exposed to (a) 0.1N HCl for 2 hours (fasted state) or (b) FeSSGF at pH 5 for 4 hours (fed state), and then to Hanks buffer at pH 6.8 for 10 hours (only the Hanks buffer stage is presented);

FIG. 13 is a graph comparing drug release as a function of time from 1200 mg 5ASA tablets coated with an isolation layer of HPMC and an outer layer of 30:70 starch:Eudragit® S applied from an aqueous coating preparation (Comparative Example 8) when exposed to (a) 0.1N HCl for 2 hours (fasted state) or (b) FeSSGF at pH 5 for 4 hours (fed state), and then to Hanks buffer at pH 6.8 for 10 hours (only the Hanks buffer stage is presented);

FIG. 14 is a graph comparing drug release as a function of time from 1200 mg 5ASA tablets coated with an isolation layer of HPMC, an inner layer of neutralized Eudragit® S and an outer layer of 50:50 starch: Eudragit® S applied from a "semi organic" coating preparation (Example 6) when exposed to (a) 0.1N HCl for 2 hours (fasted state) or (b) FeSSGF at pH 5 for 4 hours (fed state), and then to Hanks buffer at pH 6.8 for 10 hours (only the Hanks buffer stage is presented);

FIG. 15 is a graph comparing drug release as a function of time from 400 mg 5ASA tablets coated with an isolation layer of HPMC, an inner layer of neutralized Eudragit® S and an outer layer of 30:70 starch: Eudragit® S applied from a "semi organic" coating preparation (Example 7) when exposed to (a) 0.1N HCl for 2 hours (fasted state) or (b) FeSSGF at pH 5 for 4 hours (fed state), and then to Hanks buffer at pH 6.8 for 10 hours (only the Hanks buffer stage is presented);

FIG. 16 is a graph comparing drug release as a function of time from 400 mg 5ASA tablets coated with an inner layer of neutralized Eudragit® S and an outer layer of 30:70 starch: Eudragit® S applied from a "semi organic" coating preparation (Example 1) when exposed to (a) 0.1N HCl for 2 hours (fasted state) or (b) FeSSGF at pH 5 for 4 hours (fed state), and then to Hanks buffer at pH 6.8 for 10 hours (only the Hanks buffer stage is presented); and

MATERIALS 5-aminosalicylic acid (mesalazine EP) was purchased from Cambrex Karlskoga AB, Karlskoga, Sweden. Lactose (Tablettose 80) was purchased from Meggle, Hamburg, Germany. Sodium starch glycolate (Explotab™) was purchased from JRS Pharma, Rosenberg, Germany. Talc was purchased from Luzenac Deutschland GmbH, Dusseldorf, Germany. Polyvinylpyrolidon (PVP) was purchased from ISP Global Technologies, Köln, Germany. Magnesium stearate was purchased from Peter Greven GmbH, Bad Münstereifel, Germany. Eudragit® S 100, Eudragit® L 30 D-55 and Eudragit® FS 30 D were all purchased from Evonik GmbH, Darmstadt, Germany. Maize starch (NI-460 and Eurylon VI or 6) was purchased from Roquette, Lestrem, France. Polysorbate 80, butan-1-ol and sodium hydroxide were all purchased from Sigma-Aldrich, Buchs, Switzerland. Potassium dihydrogen phosphate, glyceryl monostearate (GMS), triethyl citrate (TEC) and ammonia solution (25%) were all purchased from VWR International LTD, Poole, UK.

Preparation of 400 mg 5ASA Tablet Cores

Oblong shaped 400 mg 5ASA tablet cores with dimensions 14.5×5.7 mm were prepared by fluid bed granulation followed by blending and compression. Each tablet contained 76.9 wt % 5ASA (400 mg; drug); 14.7 wt % lactose (filler); 1.7 wt % PVP (binder); 3.5 wt % sodium starch glycolate (disintegrant); and 2 wt % talc and 1.2 wt % magnesium stearate (lubricants).

The obtained tablet cores were coated as discussed below in Examples 1, 8 and 9, and in Comparative Examples 1 to 3 and 9.

Preparation of 1200 mg 5ASA Tablet Cores

Oblong-shaped 1200 mg 5ASA tablet cores (having dimensions 21×10 mm) were prepared by wet granulation. Each tablet contained 85.7 wt % 5ASA (1200 mg), 9.2 wt % microcrystalline cellulose, 1.7 wt % HPMC, 2.9 wt % sodium starch glycolate, and 0.5 wt % magnesium stearate.

The obtained tablet cores were coated as discussed below in Examples 2 to 7 and 10, and in Comparative Examples 4 to 7.

Example 1 (Inner Layer of Neutralised Eudragit® S/Outer Layer of 70:30 Mixture of Eudragit® S and Starch)

Inner Layer

The inner coating layer was applied using an aqueous preparation of Eudragit® S 100, where the pH is adjusted to pH 8. The composition of the inner layer also includes 50% of triethyl citrate (based on dry polymer weight), 10% potassium dihydrogen phosphate (based on dry polymer weight), 10% glyceryl monostearate (GMS; based on dry polymer weight) and 40% polysorbate 80 (based on GMS weight). The pH was adjusted using 1M NaOH until the pH 8 was obtained. Potassium dihydrogen phosphate and triethyl citrate were dissolved in distilled water, followed by dispersion of the Eudragit® S 100 under mechanical agitation. The pH of the dispersion was then adjusted to pH 8 with 1M NaOH and left mixing for 1 hour.

A GMS dispersion was prepared at a concentration of 10% w/w. Polysorbate 80 (40% based on GMS weight) was dissolved in distilled water followed by dispersion of the GMS. The dispersion was then heated to 75° C. for 15 minutes under strong magnetic stirring in order to form an emulsion. The emulsion was cooled at room temperature and under stirring.

The GMS dispersion was added to the neutralised Eudragit® S 100 solution and the final preparation was coated on to 400 mg 5ASA tablet cores, using a fluid bed spray coating machine until the coating amount reached 5 mg polymer/cm². The total solids content of the coating solution is 10%. The coating parameters were as follows: spraying rate 20 ml/min/kg tablets, atomizing pressure 0.2 bar and inlet air temperature 40° C.

Outer Layer

The outer coating layer was applied from a mixture of aqueous starch dispersion and an organic Eudragit® S 100 solution.

The aqueous starch dispersion was prepared by dispersing maize starch into butan-1-ol, followed by water, under magnetic stirring. The ratio of maize starch:butan-1-ol:water was 1:2:22. The resulting dispersion was heated to boiling and then cooled under stirring overnight. The % solids content of the cooled preparation was calculated based on the final weight of the dispersion (considering the evaporation during heating).

The organic Eudragit® S 100 solution was prepared by dissolving Eudragit® S 100 in 96% ethanol under high speed stirring. The final solution contained about 6% polymer solids. The starch dispersion was added dropwise to the Eudragit® S 100 solution to obtain a ratio of starch:Eudragit® S of 30:70. The mixture was mixed for 2 hours and 20% triethyl citrate (based on total polymer weight) and 5% glyceryl monostearate (GMS, based on total polymer weight) were added and mixed for further 2 hours.

The GMS was added in the form of a dispersion prepared at a concentration of 5% w/w. Polysorbate 80 (40% based on GMS weight) was dissolved in distilled water followed by dispersion of the GMS. This dispersion was then heated to 75° C. for 15 minutes under strong magnetic stirring in order to form an emulsion. The emulsion was cooled at room temperature and under stirring.

The final preparation was coated on to 5ASA tablet cores, previously coated with the inner coating layer, using a fluid bed spray coating machine until a coating having 7 mg total polymer/cm² was obtained. The spray coating parameters were as follows: spraying rate 14 ml/min/kg tablets, atomizing pressure 0.2 bar and inlet air temperature 40° C.

Example 2 (Isolation Layer/Inner Layer of Neutralised Eudragit® L30D-55/Outer Layer of 70:30 Mixture of Eudragit® S and Starch)

Isolation Layer

An isolation layer was used containing a mixture of HPMC and 20% polyethylene glycol 6000 (PEG 6000), based on dry polymer weight.

The HPMC was dissolved in water under magnetic stirring and then the PEG 6000 was added to form a coating preparation. The coating preparation was sprayed onto the 1200 mg 5ASA cores, using a pan-coating machine to achieve a coating amount of 3 mg polymer/cm² to form isolation layer coated tablets.

The coating parameters were as follows: Spray rate 3.1 g/min per kg tablet cores; atomizing pressure 0.7 bar; inlet air volume 19 m³/h per kg tablet cores; and product temperature 35° C.

Inner Layer

The inner layer was applied from an aqueous coating preparation of Eudragit® L30D-55, where the pH had been adjusted to pH 8. The composition of the inner layer also included 20% TEC (based on dry polymer weight), 1% potassium dihydrogen phosphate (based on dry polymer weight) and 50% talc (based on dry polymer weight). The pH was adjusted using 1M NaOH until pH 8 is obtained.

Potassium dihydrogen phosphate and TEC were dissolved in distilled water for 15 minutes, after which an Eudragit® L30D-55 dispersion was added under mechanical agitation and mixed for 15 minutes. The pH was then adjusted to pH 8 with 1M NaOH and the solution was left stirring for 1 hour. Talc was then added to the solution and mixing continued for a further 30 minutes to form the inner coating preparation. The inner coating preparation was coated onto the isolation layer coated tablets, using a pan-coating machine until the coating amount reached 5 mg polymer/cm² to form inner layer coated tablets. The total solids content of the inner coating preparation was 10% (by weight).

As used herein, the "total solids content" of a suspension, dispersion or other preparation is the total weight of solids used to form the preparation as a proportion of the total weight of the preparation (solids and solvent). The skilled reader would appreciate that dissolution of a portion of the solids into the solvent does not affect the total solids content of the preparation.

The coating parameters were as follows: Spray rate 6.75 g/min per kg tablet cores; atomizing pressure 0.6 bar; inlet air volume 75 m³/h per kg tablet cores; and product temperature 31° C.

Outer Layer

The outer layer was applied from a mixture of an aqueous starch dispersion and an aqueous Eudragit® S 100 solution.

The aqueous starch dispersion was prepared by dispersing maize starch into butan-1-ol, followed by water, under magnetic stirring. The ratio of maize starch:butan-1-ol:water was 1:2:22. The resulting dispersion was heated to boiling under reflux and then cooled under stirring overnight.

The aqueous Eudragit® S 100 solution was prepared by dispersing Eudragit® S 100 in water under high speed stirring followed by partial (15-20%) neutralization with 1N ammonia solution (obtained by dilution of 25% ammonia solution).

The aqueous Eudragit® S 100 solution was added to the starch dispersion to obtain a ratio of starch:Eudragit® S of 30:70. The mixture was stirred for 1 hour and 60% TEC (based on Eudragit® S polymer weight), 50% talc (based on Eudragit® S polymer weight), 13.18% iron oxide red (based on Eudragit® S polymer weight) and 2.27% iron oxide yellow (based on Eudragit® S polymer weight) were added and mixed for further 30 minutes.

The final preparation was sprayed onto inner layer coated tablets, in a pan-coating machine until 7.14 mg total polymer/cm² was obtained to produce the coated tablets of Example 2.

The coating parameters were as follows: Spray rate 6.175 g/min per kg tablet cores; atomizing pressure 0.4 bar; inlet air volume 100 m³/h per kg tablet cores; and product temperature 35° C.

Example 3 (Isolation Layer/Inner Layer of Neutralised Eudragit® L30D-55/Outer Layer of 1:3 Mixture of Eudragit® L30D-55 and Guar Gum)

Isolation Layer

The isolation layer is formed by a mixture of HPMC and 20% polyethylene glycol 6000 (PEG 6000), based on dry polymer weight.

The HPMC polymer was dissolved in water under magnetic stirring and then PEG 6000 was added to form an isolation layer coating preparation. The coating preparation was sprayed onto 1200 mg 5ASA tablet cores, using a pan-coating machine to achieve a coating amount of 3 mg polymer/cm² to form isolation layer coated tablets.

The coating parameters were as follows: Spray rate 2.7 g/min. per kg tablet cores; atomizing pressure 0.7 bar; inlet air volume 16 m³/h per kg tablet cores; and product temperature 35° C.

Inner Layer

The inner layer is applied from an aqueous preparation of Eudragit L30D-55, where the pH is adjusted to pH 8. The composition of the inner layer also includes 20% TEC (based on dry polymer weight), 1% potassium dihydrogen phosphate (based on dry polymer weight), and 50% talc (based on dry polymer weight). The pH is adjusted using 1M NaOH until pH 8 is obtained.

Potassium dihydrogen phosphate and TEC were dissolved in distilled water with stirring for 15 minutes, after which Eudragit L30D-55 dispersion was added under mechanical agitation and mixed for 15 minutes. The pH was then adjusted to pH 8 with 1M NaOH and the solution was left mixing for 1 hour. Talc was then added and mixing was continued for a further 30 minutes to form the inner layer coating preparation. The inner layer coating preparation was coated onto the isolation layer coated tablets using a pan-coating machine until the coating amount reached 5 mg polymer/cm² to form inner layer coated tablets. The total solids content of the final preparation is 10%.

The coating parameters were as follows: Spray rate 2.7 g/min. per kg tablet cores; atomizing pressure 0.6 bar; inlet air volume 30 m³/h per kg tablet cores; and product temperature 31° C.

Outer Layer

The outer layer is applied from a mixture of Eudragit® L30D-55 and guar gum.

Eudragit L30D-55 was dissolved in isopropanol. Guar gum was dispersed with talc in a mixture of water and isopropanol (50:50) for 15 minutes followed by homogenization for 5 minutes. The Eudragit L30D-55 solution was then added to the guar gum dispersion and the resultant mixture was stirred for 20 minutes to form the outer layer coating preparation. The coating preparation was sprayed onto inner layer coated tablets, in a pan-coating machine until the coating amount reached 9.71 total polymer/cm² (weight ratio of 1:3 of the dry substances). The coated tablets were dried at 40° C. for 2 hours to form the tablets of Example 3.

The coating parameters were as follows: Spray rate 8.0 g/min per kg tablet cores; atomizing pressure 0.6 bar; inlet air volume 75 m³/h per kg tablet cores; and product temperature 29° C.

Example 4 (Isolation Layer/Inner Layer of PVA with Buffer and Base/Outer Layer of a 70:30 Mixture of Eudragit® S & FS Blend (50:50) and Starch)

Isolation Layer

The isolation layer is composed of polyvinyl alcohol or PVA (Opadry 85F).

The polymer was suspended in water under magnetic stirring to achieve a concentration of 10% solids of the final weight of the dispersion to form an isolation layer coating preparation.

The coating preparation was sprayed onto 1200 mg 5ASA tablet cores, using a pan-coating machine to achieve a coating amount of 2%, based on the weight of the uncoated tablets to form isolation layer coated tablets.

The coating parameters were as follows: Spray rate 6.45 g/min per kg tablets; atomizing pressure 0.6 bar; inlet air volume 62.5 m³/h per kg tablet cores; and product temperature 40° C.

Inner Layer

The inner layer is composed of polyvinyl alcohol (Opadry 85F) and 20% potassium dihydrogen phosphate (based on Opadry 85F).

Potassium dihydrogen phosphate was dissolved in water under magnetic stirring and then the polyvinyl alcohol (Opadry 85F) was added to form a suspension. The pH of the suspension was then adjusted to pH 8 with 1M NaOH and the mixture was left stirring for 1 hour to form an inner layer coating preparation. The coating preparation was sprayed onto isolation layer coated tablets using a pan-coating machine until the coating amount reached 2%, based on the weight of the uncoated tablets, to form inner layer coated tablets.

The coating parameters were as follows: Spray rate 8.2 g/min per kg tablet cores; atomizing pressure 0.7 bar; inlet air volume 62.5 m³/h per kg tablet cores; and product temperature 40° C.

Outer Layer

The outer layer formulation is applied from a mixture of an aqueous starch dispersion and an aqueous dispersion of a 50:50 blend (based on dry polymer) of Eudragit® S 100 and Eudragit® FS 30D.

The aqueous starch dispersion was prepared by dispersing maize starch (Eurylon 6) into butan-1-ol under magnetic stirring. Water was added while stirring was continued. The ratio of maize starch:butan-1-ol:water was 1:2:22. The resulting dispersion was heated to boiling under reflux and then cooled under stirring overnight.

An aqueous dispersion of Eudragit® S 100 was prepared by dispersing Eudragit® S 100 in water under high speed stirring followed by partial (15-20%) neutralization with 1N ammonia (formed by dilution of 25% ammonia solution) TEC was added to the dispersion and mixed for 30 minutes. Eudragit® FS 30D was added to form a 50:50 blend with the Eudragit® S 100 and mixing was continued for a further 30 minutes.

The starch dispersion was added into the dispersion of the Eudragit® S 100/Eudragit® FS 30D blend and the mixture was stirred for a further 30 minutes. The mixture contained a ratio of starch:Eudragit S 100/Eudragit FS 30D blend of 30:70.

A suspension of 50% talc (based on Eudragit® polymer weight), 13.18% iron oxide red (based on Eudragit® polymer weight) and 2.27% iron oxide yellow (based on Eudragit® polymer weight) in water was formed under high shear homogenization and this suspension was added to the starch/Eudragit® blend mixture and mixing was continued for a further 30 minutes to form an outer layer coating preparation.

The coating preparation was sprayed onto inner layer coated tablets in a pan-coating machine until 5.2 mg Eudragit® polymer blend/cm² was obtained to form the tablets of Example 4.

The coating parameters were as follows: Spray rate 8.5 g/min per kg tablet cores; atomizing pressure 0.7 bar; inlet air volume 62.5 m³/h per kg tablet cores; and product temperature 41° C.

Example 5 (Isolation Layer/Inner Layer of Neutralised Eudragit® S/Outer Layer of 70:30 Mixture of Eudragit® S and Starch)

Isolation Layer

The isolation layer was formed as in Example 3 although the coating parameters were as follows: Spray rate 2.33 g/min. per kg tablet cores; atomizing pressure 0.7 bar; inlet air volume 16.3 m³/h per kg tablet cores; and product temperature 33° C.

Inner Layer

The inner coating layer was formed as in Example 1 with the exceptions that the composition of the inner layer included 70% (not 50%) of triethyl citrate (based on dry polymer weight) and 1% (not 10%) potassium dihydrogen phosphate (based on dry polymer weight), that the coating preparation was coated onto the isolation layer coated 1200 mg tablets using a perforated pan coater machine, and that the coating parameters were as follows: spraying rate 2.9 g/min/kg tablets, atomizing pressure 0.6 bar, inlet air volume was 16.3 m³/h/kg tablets and the product temperature was 33° C.

Outer Layer

The outer coating layer was formed as in Example 1 with the exceptions that 13.18% iron oxide red (based on Eudragit polymer weight) and 2.27% iron oxide yellow (based on Eudragit polymer weight) were suspended in ethanol under high shear homogenisation and this suspension was added into the starch and Eudragit mixture and the resultant mixed for the further 30 minutes prior to the addition of the GMS, that the coating preparation was applied onto the inner layer coated 1200 mg 5ASA tablets using a perforated pan coater machine, and that the spray coating parameters were as follows: spraying rate 3.1 g/min/kg tablets, atomising pressure 0.4 bar, inlet air volume 21.7 m³/h/kg tablets and product temperature 34° C.

Example 6 (Isolation Layer/Inner Layer of Neutralised Eudragit® S/Outer Layer of 50:50 Mixture of Eudragit® S and Starch)

Isolation Layer

The isolation layer was formed on 1200 mg 5ASA tablets cores as described in Example 3.

Inner Layer

The inner layer was formed on isolation layer coated 1200 mg 5ASA tablet cores as described in Example 5.

Outer Layer

The outer coating layer was formed on inner layer coated 5ASA tablet cores as described in Example 5 with the exceptions that the ratio of maize starch:butan-1-ol:water was 1:1:~9.5, that the starch:Eudragit S ratio was 50:50, and that the spray parameters were as follows: spraying rate 7.4 g/min/kg tablets, atomising pressure 0.4 bar, inlet air volume 40 m³/h/kg tablets and product temperature 34° C.

Example 7 (Isolation Layer/Inner Layer of Neutralised Eudragit® S/Outer Layer of 70:30 Mixture of Eudragit® S and Starch)

Isolation Layer

The isolation layer was applied to 400 mg 5ASA tablet cores using the procedure described in Example 3 with the exceptions that a fluid bed spray coater was used and the coating parameters were as follows: spraying rate 3.1 g/min/kg tablets, atomising pressure 0.2 bar, and inlet air temperature 40° C.

Inner Layer

The inner coating layer was applied in the same manner as described in Example 1 with the exception that the composition of the inner layer included 70% (not 50%) of triethyl citrate (based on dry polymer weight) and 1% (not 10%) potassium dihydrogen phosphate (based on dry polymer weight). In addition, the inner coating layer preparation was coated on to the isolation layer coated 400 mg 5ASA tablet cores.

Outer Layer

The outer coating layer was formed as in Example 1 with the exceptions that 13.18% iron oxide red (based on Eudragit polymer weight) and 2.27% iron oxide yellow (based on Eudragit polymer weight) were suspended in ethanol under high shear homogenisation and this suspension was added into the starch and Eudragit mixture and the resultant mixed for the further 30 minutes prior to the addition of the GMS, and that the outer coating layer preparation was coated on to the inner layer coated 400 mg 5ASA tablet cores. The coating parameters were as follows: spraying rate 11 ml/min/kg tablets, atomising pressure 0.2 bar, and inlet air temperature 40° C.

Comparative Example 1 (Single-Layer Coating of Eudragit® S)

The coating layer containing Eudragit® S 100 was applied as an organic coating composition. The coating composition contained 20% triethyl citrate (based on dry polymer weight), 10% glyceryl monostearate (based on dry polymer weight) and 40% polysorbate 80 (based on GMS weight). Briefly, triethyl citrate was dissolved in 96% ethanol followed by Eudragit® S 100 under mechanical stirring and mixing continued for 1 hour.

The GMS was added in the form of a dispersion prepared at a concentration of 10% w/w. Polysorbate 80 (40% based on GMS weight) was dissolved in distilled water followed by dispersion of GMS. This preparation was then heated to 75° C. for 15 minutes under strong magnetic stirring in order to form an emulsion. The emulsion was cooled at room temperature and under stirring.

The GMS dispersion was added to the organic Eudragit® S solution and the final coating solution was coated on to the 5ASA tablet cores, using a fluid bed spray coating machine to achieve a coating amount of 5 mg polymer/cm². The coating parameters were as follows: spraying rate 16 ml/min/kg tablets, atomizing pressure 0.2 bar and inlet air temperature 40° C.

Comparative Example 2 (Single-Layer Coating of a 70:30 Mixture of Eudragit® S and Starch)

The coating layer composition contains a mixture of an aqueous starch dispersion and an organic Eudragit® S 100 solution. The aqueous starch dispersion was prepared by dispersing maize starch into butan-1-ol, followed by water, under magnetic stirring. The ratio of maize starch:butan-1-ol:water was 1:2:22. The resulting dispersion was heated to boiling and then cooled under stirring overnight. The % solids content of the cooled preparation was calculated based on the final weight of the dispersion (considering the evaporation during heating).

The organic Eudragit® S solution was prepared by dissolution of Eudragit® S 100 in 96% ethanol under high speed stirring. The final solution contained about 6% polymer solids. The starch dispersion was added dropwise to the Eudragit® S 100 solution to obtain a ratio of starch:Eudragit S of 30:70. The mixture was mixed for 2 hours and 20% triethyl citrate (based on total polymer weight) and 5% glyceryl monostearate (based on total polymer weight) were added and the mixture was mixed for further 2 hours.

The GMS was added in the form of a dispersion prepared at a concentration of 5% w/w. Polysorbate 80 (40% based on GMS weight) was dissolved in distilled water followed by dispersion of GMS. This preparation was then heated to 75° C. for 15 minutes under strong magnetic stirring in order to form an emulsion. The emulsion was cooled at room temperature and under stirring.

The final preparation was coated on to the 5ASA tablet cores in a fluid bed spray coating machine until a 7 mg Eudragit® S polymer/cm$^2$ was obtained. The spray coating parameters were as follows: spraying rate 14 ml/min/kg tablets, atomizing pressure 0.2 bar and inlet air temperature 40° C.

Comparative Example 3 (Inner Layer of Neutralised Eudragit® S/Outer Layer of Eudragit® S)

Inner Layer

The inner coating layer is composed by an aqueous preparation of Eudragit® S 100, where the pH is adjusted to pH 8. The composition of the inner layer also includes 50% of triethyl citrate (based on dry polymer weight), 10% potassium dihydrogen phosphate (based on dry polymer weight), 10% glyceryl monostearate (based on dry polymer weight) and 40% polysorbate 80 (based on GMS weight). The pH was adjusted using 1M NaOH until the pH 8 is obtained. Potassium dihydrogen phosphate and triethyl citrate were dissolved in distilled water, followed by dispersion of the Eudragit® S 100 under mechanical agitation. The pH was then adjusted to pH 8 with 1M NaOH and left mixing for 1 hour.

A GMS dispersion was prepared at a concentration of 10% w/w. Polysorbate 80 (40% based on GMS weight) was dissolved in distilled water followed by dispersion of GMS. This preparation was then heated to 75° C. for 15 minutes under strong magnetic stirring in order to form an emulsion. The emulsion was cooled at room temperature and under stirring.

The GMS dispersion was added to the neutralised Eudragit® S solution and the final preparation was coated on to 5ASA tablet cores, using a fluid bed spray coating machine until the coating amount reached 5 mg polymer/cm$^2$. The total solids content of the coating solution is 10%. The coating parameters were as follows: spraying rate 20 ml/min/kg tablets, atomizing pressure 0.2 bar and inlet air temperature 40° C.

Outer Layer

The outer coating layer is composed of Eudragit® S 100, applied as an organic solution. The coating solution contains 20% triethyl citrate (based on dry polymer weight), 10% glyceryl monostearate (based on dry polymer weight) and 40% polysorbate 80 (based on GMS weight). Briefly, triethyl citrate was dissolved in 96% ethanol followed by Eudragit® S 100 under mechanical stirring and mixing continued for 1 hour.

A GMS dispersion was prepared at a concentration of 10% w/w. Polysorbate 80 (40% based on GMS weight) was dissolved in distilled water followed by dispersion of the GMS. This dispersion was then heated to 75° C. for 15 minutes under strong magnetic stirring in order to form an emulsion. The emulsion was cooled at room temperature and under stirring.

The GMS preparation was added to the Eudragit® S 100 solution and the final coating solution was coated on to 5ASA tablet cores, previously coated with the inner coating layer, using a fluid bed spray coating machine to achieve a coating amount of 5 mg Eudragit® S polymer/cm$^2$. The coating parameters were as follows: spraying rate 16 ml/min/kg tablets, atomizing pressure 0.2 bar and inlet air temperature 40° C.

Comparative Example 4 (Isolation Layer/Inner Layer of Eudragit® L30D-55/Outer Layer of a 70:30 Mixture of Eudragit® S/Starch)

Isolation Layer

The isolation layer is formed from a mixture of HPMC and 20% polyethylene glycol 6000 (PEG6000), based on dry polymer weight.

The polymer was dissolved in water under magnetic stirring and then PEG6000 was added to form the isolation layer coating preparation. The coating preparation was sprayed onto 1200 mg 5ASA tablet cores, using a pan-coating machine to achieve a coating amount of 3 mg polymer/cm$^2$ to form isolation layer coated tablets.

The coating parameters were as follows: Spray rate 2.7 g/min. per kg tablet cores; atomizing pressure 0.7 bar; inlet air volume 16 m$^3$/h per kg tablet cores; and product temperature 35° C.

Inner Layer

The inner layer is made from a standard (non-neutralised) aqueous preparation of Eudragit L30D-55. The composition of the inner layer also includes 20% TEC (based on dry polymer weight) and 50% talc (based on dry polymer weight).

Eudragit L30D-55 was diluted in distilled water and then TEC and a talc suspension were added and mixed for 1 hour to form the inner layer coating preparation. The coating preparation was coated onto isolation layer coated tablets using a pan-coating machine until the coating amount reached 5 mg polymer/cm$^2$ to form inner layer coated tablets. The total solids content of the final preparation is 10%.

The coating parameters were as follows: Spray rate 6.125 g/min per kg tablet cores; atomizing pressure 0.6 bar; inlet air volume 100 m$^3$/h per kg tablet cores; and product temperature 33° C.

Outer Layer

The outer layer is made from a mixture of aqueous starch dispersion and an aqueous Eudragit® S 100 re-dispersion.

The aqueous starch dispersion was prepared by dispersing maize starch into butan-1-ol, followed by water, under magnetic stirring. The ratio of maize starch:butan-1-ol:water was 1:2:22. The resulting dispersion was heated to boiling under reflux and then cooled under stirring overnight.

The aqueous Eudragit® S re-dispersion was prepared by dispersing Eudragit® S 100 in water under high speed stirring followed by partial (15-20%) neutralization with 1N ammonia (obtained by dilution of 25% ammonia solution).

The aqueous Eudragit® S re-dispersion was added to the starch dispersion to obtain a ratio of starch:Eudragit S of 30:70. The mixture was stirred for 1 hour and 60% TEC (based on Eudragit® S polymer weight), 50% talc (based on Eudragit® S polymer weight), 13.18% iron oxide red (based on Eudragit® S polymer weight) and 2.27% iron oxide yellow (based on Eudragit® S polymer weight) were added and the mixture was stirred for a further 30 minutes to form an outer layer coating preparation. The outer layer coating preparation was sprayed onto inner layer coated tablets, in a pan-coating machine until 7.14 mg total polymer/cm$^2$ was obtained to produce the tablets of Comparative Example 4.

The coating parameters were as follows: Spray rate 10.0 g/min; atomizing pressure 0.4 bar; inlet air volume 100 m³/h per kg tablet cores; and product temperature 35° C.

Comparative Example 5 (Isolation Layer/Inner Layer of Eudragit L30D-55/Outer Layer of a 1:3 Mixture of Eudragit L30D-55/Guar Gum)

Isolation Layer

The isolation layer is applied from a mixture of HPMC and 20% polyethylene glycol 6000 (PEG 6000), based on dry polymer weight.

The HPMC polymer was dissolved in water under magnetic stirring and then PEG 6000 was added to form the isolation layer coating preparation. The coating preparation was sprayed onto 1200 mg 5ASA tablet cores using a pan-coating machine to achieve a coating amount of 3 mg polymer/cm² to form isolation layer coated tablets.

The coating parameters were as follows: Spray rate 2.7 g/min per kg tablet cores; atomizing pressure 0.7 bar; inlet air volume 16 m³/h per kg tablet cores; and product temperature 35° C.

Inner Layer

The inner layer was applied from a standard (non-neutralised) aqueous preparation of Eudragit L30D-55. The composition of the inner layer also included 20% TEC (based on dry polymer weight) and 50% talc (based on dry polymer weight).

Eudragit L30D-55 was diluted in distilled water and then TEC and talc were added to form a mixture which was stirred for 1 hour to form an inner layer coating preparation. The coating preparation was coated onto isolation layer coated tablets using a pan-coating machine until the coating amount reached 5 mg polymer/cm² to form inner layer coated tablets. The total solids content of the final preparation is 10% based on the final weight of the suspension.

The coating parameters were as follows: Spray rate 2.45 g/min per kg tablet cores; atomizing pressure 0.6 bar; inlet air volume 25 m³/h per kg tablet cores; and product temperature 33° C.

Outer Layer

The outer layer contains a mixture of Eudragit L30D-55 and guar gum.

Eudragit L30D-55 was dissolved in isopropanol, and guar gum was dispersed with talc in a mixture of water and isopropanol (50.50) for 15 minutes followed by homogenization for 5 minutes. The Eudragit L30D-55 solution was then added to the guar gum dispersion and stirred for 20 minutes to form an outer layer coating preparation. The coating preparation was sprayed onto inner layer coated tablets in a pan-coating machine until 9.71 total polymer/cm² (weight ratio of 1:3 of the dry substances) was obtained. The coated tablets were dried at 40° C. for 2 hours to form the tablets of Comparative Example 5.

The coating parameters were as follows: Spray rate 8.0 g/min per kg tablet cores; atomizing pressure 0.6 bar; inlet air volume 75 m³/h per kg tablet cores; and product temperature 29° C.

Comparative Example 6 (Isolation Layer/Outer Layer of a 70:30 Mixture of Eudragit® S & FS Blend (50:50) and Starch)

Isolation Layer

The isolation layer was composed of polyvinyl alcohol (Opadry 85F).

The polyvinyl alcohol (Opadry 85F) was suspended in water under magnetic stirring to achieve a concentration of 10% solids based on the final weight of the suspension to form an isolation layer coating preparation.

The coating preparation was sprayed onto 1200 mg 5ASA tablet cores using a pan-coating machine to achieve a coating amount of 2%, based on the weight of the uncoated tablets, to form isolation layer coated tablets.

The coating parameters were as follows: Spray rate 6.45 g/min per kg tablets; atomizing pressure 0.6 bar; inlet air volume 62.5 m³/h per kg tablet cores; and product temperature 40° C.

Outer Layer

The outer layer formulation is applied from a mixture of an aqueous starch dispersion and an aqueous dispersion of a 50:50 blend (based on dry polymer) of Eudragit® S 100 and Eudragit® FS 30D.

The aqueous starch dispersion was prepared by dispersing maize starch (Eurylon 6) into butan-1-ol under magnetic stirring. Water was added while stirring was continued. The ratio of maize starch:butan-1-ol:water was 1:2:22. The resulting dispersion was heated to boiling under reflux and then cooled under stirring overnight.

An aqueous dispersion of Eudragit® S 100 was prepared by dispersing Eudragit® S 100 in water under high speed stirring followed by partial (15-20%) neutralization with 1N ammonia (formed by dilution of 25% ammonia solution) TEC was added to the dispersion and mixed for 30 minutes. Eudragit® FS 30D was added to form a 50:50 blend with the Eudragit® S 100 and mixing was continued for a further 30 minutes.

The starch dispersion was added into the dispersion of the Eudragit® S 100/Eudragit® FS 30D blend and the mixture was stirred for a further 30 minutes. The mixture contained a ratio of starch:Eudragit S 100/Eudragit FS 30D blend of 30:70.

A suspension of 50% talc (based on Eudragit® polymer weight), 13.18% iron oxide red (based on Eudragit® polymer weight) and 2.27% iron oxide yellow (based on Eudragit® polymer weight) in water was formed under high shear homogenization and this suspension was added to the starch/Eudragit® blend mixture and mixing was continued for a further 30 minutes to form an outer layer coating preparation.

The coating preparation was sprayed onto isolation layer coated tablets in a pan-coating machine until 5.2 mg Eudragit® polymer blend/cm² was obtained to form the tablets of Example 4.

The coating parameters were as follows: Spray rate 8.5 g/min per kg tablet cores; atomizing pressure 0.7 bar; inlet air volume 62.5 m³/h per kg tablet cores; and product temperature 41° C.

Comparative Example 7 (Isolation Layer/Outer Layer of 30:70 Starch:Eudragit S)

Isolation Layer

Isolation layer coated 1200 mg 5ASA tablet cores were prepared as in Comparative Example 4.

Outer Layer

The outer coating layer was applied to the inner coated tablet cores from a mixture of aqueous starch dispersion and an organic Eudragit® S 100 solution.

The aqueous starch dispersion was prepared by dispersing maize starch into butan-1-ol, followed by water, under magnetic stirring. The ratio of maize starch:butan-1-ol:water was 1:2:22. The resulting dispersion was heated to boiling and then cooled under stirring overnight. The % solids content of the cooled preparation was calculated based on the final weight of the dispersion (considering the evaporation during heating).

The organic Eudragit® S 100 solution was prepared by dissolving Eudragit® S 100 in 96% ethanol under high speed stirring. The final solution contained about 6% polymer solids. The starch dispersion was added dropwise to the Eudragit® S 100 solution to obtain a ratio of starch:Eudragit® S of 30:70.

The mixture was mixed for 2 hours and 20% triethyl citrate (based on total polymer weight) and 5% glyceryl monostearate (GMS, based on total polymer weight) were added and mixed for further 2 hours. 13.18% iron oxide red (based on Eudragit polymer weight) and 2.27% iron oxide yellow (based on Eudragit polymer weight) were suspended in ethanol under high shear homogenization and this suspension was added into the starch and Eudragit mixture and mixed for further 30 minutes.

The GMS was added in the form of an emulsion prepared at a concentration of 5% w/w. Polysorbate 80 (40% based on GMS weight) was dissolved in distilled water followed by dispersion of the GMS. This dispersion was then heated to 75° C. for 15 minutes under strong magnetic stirring in order to form an emulsion. The emulsion was cooled at room temperature and under stirring. The final preparation was coated onto the isolation layer coated tablet cores using a perforated pan coater machine until a coating having 5 mg Eudragit® S polymer/cm$^2$ was obtained. The spray coating parameters were as follows: spraying rate 3.1 g/min/kg tablets, atomizing pressure 0.4 bar, inlet air volume 21.7 m$^3$/h/kg tablets and product temperature 34° C.

Comparative Example 8 (Isolation Layer/Outer Layer of 30:70 Starch:Eudragit S)

Isolation layer coated 1200 mg 5ASA tablet cores were prepared as in Comparative Example 4.
Outer Layer The outer layer is applied from a mixture of an aqueous starch dispersion and an aqueous Eudragit S 100 re-dispersion.

The aqueous starch dispersion was prepared as described in Example 1.

The aqueous Eudragit S re-dispersion was prepared by dispersing Eudragit S 100 in water under high speed stirring followed by partial neutralisation with 1N NH$_3$ obtained by dilution of 25% ammonia.

The aqueous Eudragit S re-dispersion was added to the starch dispersion to obtain a ratio of starch to Eudragit S of 30:70. This was mixed for 1 hour and 60% TEC (based on Eudragit S polymer weight), 50% talc (based on Eudragit S polymer weight), 13.18% iron oxide red (based on Eudragit S polymer weight) and 2.27% iron oxide yellow (based on Eudragit S polymer weight) were added and mixed for a further 30 minutes to form the outer layer coating preparation.

The outer layer coating preparation was sprayed on to inner layer coated 1200 mg 5ASA tablet cores in a pan coating machine until 7.14 mg total polymer/cm$^2$ was obtained. The coating parameters were as follows: spray rate 6.175 g/min·kg tablet cores, atomising pressure 0.4 bar, inlet air volume 100 m$^3$/h/kg tablet cores and product temperature 35° C.

Drug Release Test #1—Effect of pH Alone

Figure 1:
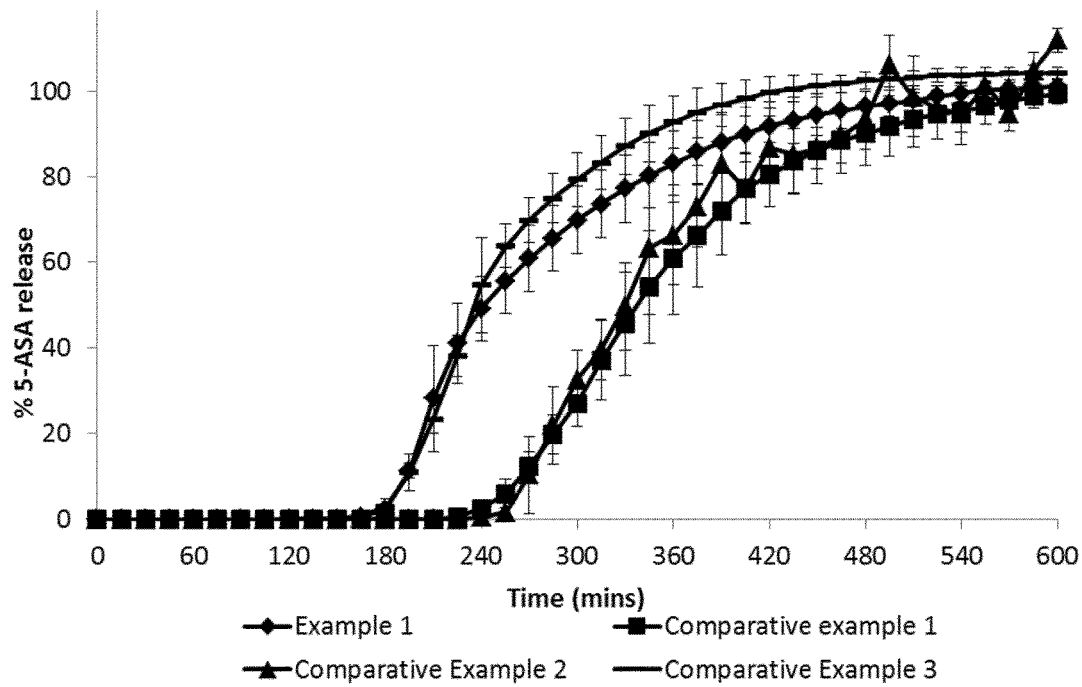

In vitro dissolution studies were performed on a USP type II apparatus using a paddle speed of 50 rpm and a media temperature of 37±0.5° C. Tablets were first tested in 0.1 M HCl for 2 hours followed by 8 or 10 hours in Krebs buffer (pH 7.4). The pH of the buffer was stabilized at 7.4±0.05 by continuously sparging with 5% CO$_2$/95% O$_2$. Absorbance measurements were taken at 5 minute intervals, with an absorbance wavelength of 301 nm in HCl and 330 nm in Krebs buffer. The composition per liter of Krebs buffer is 0.16 g of KH$_2$PO$_4$, 6.9 g of NaCl, 0.35 g KCl, 0.29 g MgSO$_4$.7H$_2$O, 0.376 g CaCl$_2$.2H$_2$O and 2.1 g NaHCO$_3$. Only the measurements taken at 15 minute intervals are depicted in FIG. 1.

Drug Release Test #2—Faecal Slurry at pH 6.8

The fermentation assays used to test the formulations were based on the method described by Hughes et al. ("In vitro fermentation of oat and barley derived beta-glucans by human faecal microbiota" FEMS Microbiol. Ecol.; 2008; 64(3); pp 482 to 493).

The basal medium used to allow bacterial growth was prepared according to Hughes et al and mixed in a ratio of 1:1 with a faecal slurry, which was prepared by homogenizing fresh human faeces (3 different donors) in phosphate buffered saline (pH 6.8) at a concentration of 40% w/w. The final concentration of the prepared faecal slurry (diluted with basal medium) was 20% w/w. The donors had not received antibiotic treatment for at least three months before carrying out the studies using the slurry.

Tablets were tested in 210 ml of faecal slurry adjusted to the required pH and under continuous stirring. The tests were carried out in an anaerobic chamber (at 37° C. and 70% RH). The samples were analysed for 5ASA content by HPLC with a UV detector.

Drug Release Test #3—Faecal Slurry at pH 6.5

As for Drug Release Test #2 but the pH of the faecal slurry was maintained at pH 6.5.

Drug Release Test #4—Dissolution in Hanks Buffer pH 6.8

In vitro dissolution studies were performed on a USP type II apparatus using a paddle speed of 50 rpm and a media temperature of 37±0.5° C. Tablets were first tested in 0.1 M HCl for 2 hours followed by 8 or 10 hours in Hanks buffer (pH 6.8). The pH of the buffer was stabilized at 6.8±0.05 by continuously sparging with 5% CO$_2$/95% O$_2$. Absorbance measurements were taken at 5 minute intervals, with an absorbance wavelength of 301 nm in HCl and 330 nm in Hanks buffer pH 6.8. The composition per liter of Hanks buffer is 0.06 g of KH$_2$PO$_4$, 0.06 g Na$_2$HPO$_4$.2H$_2$O, 8.0 g NaCl, 0.4 g KCl, 0.2 g MgSO$_4$.7H$_2$O, 0.139 g CaCl$_2$.2H$_2$O and 0.350 g NaHCO$_3$.

Drug Release Test #5—Simulated Fed/Fasted State then Hanks Buffer pH 6.8

In vitro dissolution studies were performed on a USP type II apparatus using a paddle speed of 50 rpm and a media temperature of 37±0.5° C. When simulating the "fasted" state, the studies were carried out in the manner described for Drug Release Test #4.

When simulating the "fed" state, the tablets were first tested in Fed State Simulated Gastric Fluid (FeSSGF) at pH 5.0 for 4 h followed by 10 hours in Hanks buffer (pH 6.8). The FeSSGF was as described in Jantrid et al (2008) supra.

Drug Release Test #5—40% Ethanol (v/v) in 0.1N HCl

Coated tablets were tested in a disintegration apparatus using a hydro-alcoholic solution of 0.1N HCl (40% ethanol) for 2 hours. At the end of 2 hours, the morphology of the tablets was evaluated visually for presence of cracks and/or swelling.

Results

The results presented in FIGS. 1 to 4 demonstrate that the coated tablets according to the present invention are significantly superior to the tablets of the comparative examples. In this connection, an acceleration of drug release is observed for the tablets according to the present invention, both at a pH higher (pH 7.4) than the pH threshold (pH 7) of the second polymeric material and at a lower pH (pH 6.8 or pH 6.5) than the pH threshold, relative to the comparator tablets.

In aqueous solution at pH 7.4 (drug release test #1; FIG. 1), there was no release of 5ASA from any of the tablets tested in the 2 hours that the tablets were exposed to simulated gastric conditions. However, it should be noted that, once the tablets were exposed to pH 7.4, initial release of 5ASA from Example 1 tablets occurred significantly earlier than from Comparative Example 1 (which is a conventional site-specific colonic release formulation) and from Comparative Example 2 (which is a site-specific colonic release formulation described in WO2007/122374). The profile of release of 5ASA from Example 1 closely followed that for Comparative Example 3. The similar release profiles may be explained by the similarities in the formulations themselves (Example 1 differing only in the presence of starch in the outer coating) and the absence of any colonic enzymes in the surrounding medium to digest the starch.

Figure 2:
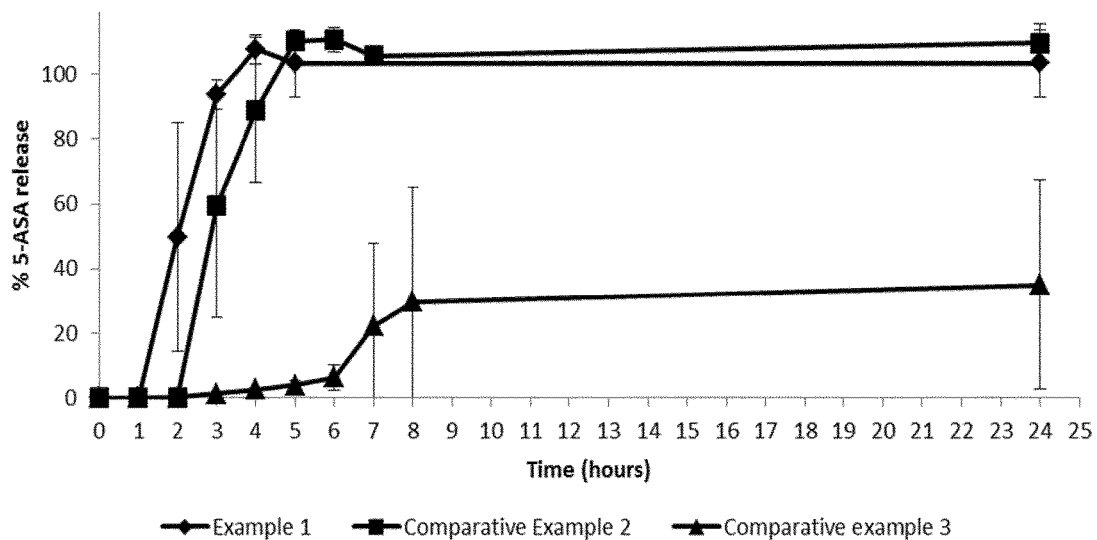

In faecal slurry at pH 6.8 (drug release test #2; FIG. 2), initial release of 5ASA from the tablets of Example 1 occurred after about 1 hour, and complete release occurred in about 3 hours after initial release. In contrast, initial release from the tablets of both Comparative Examples 2 and 3 occurred after about 2 hours, with significant release from the tablets of Comparative Example 3 occurring only after 6 hours. In addition, while the tablets of Comparative Example 2 provided complete release after about 5 hours, the tablets of Comparative Example 3 provided less than 40% release over 24 hours. The results indicate that the presence of the inner soluble layer accelerates drug release under colonic conditions from tablets having an outer layer comprising a mixture of starch and Eudragit S. The results also indicate that, without the polysaccharide in the outer layer (Comparative Example 3), release under colonic conditions is not complete.

Figure 3:
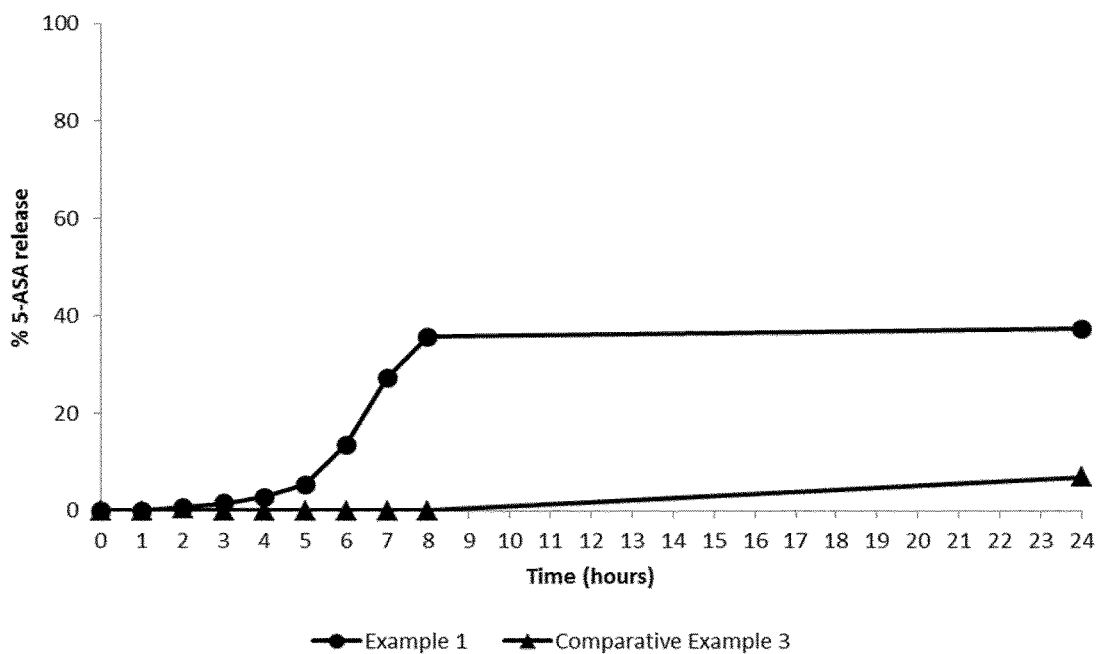
FIG. 3 is a graph comparing drug release as a function of time from 400 mg 5ASA tablets coated with (a) an inner layer of fully neutralised Eudragit® S and an outer layer of Eudragit® S (Comparative Example 3), and (b) an inner layer of fully neutralised Eudragit® S and an outer layer of a 30:70 mixture of starch and Eudragit® S (Example 1), when exposed to faecal slurry at pH 6.5 for 24 hours.

In faecal slurry at pH 6.5 (drug release test #3; FIG. 3), initial release of 5ASA from the tablets of Example 1 occurred after about 2 hours, whereas initial release from the comparator tablets occurred only after about 8 hours. In addition, even though the pH of the surrounding medium was significantly below the pH threshold of Eudragit S, tablets according to Example 1 had release about 40% of the 5ASA after about 8 hours. In contrast, the tablets of Comparative Example 3 had released less than 10% of the 5ASA after 24 hours. These results indicate that the presence of starch in the outer layer enables release of a significant amount of the active when exposed to colonic enzymes even though the pH of the surrounding medium is well below the pH threshold of the second polymeric material.

The skilled reader would appreciate that, even though the integrity of coating in Example 1 was compromised, not all of the active was released after 8 hours. The Inventors believe that this is because the test is in vitro. In vivo, the tablets would be subjected to mechanical pressure applied as a result of the motility of the colon and which should contribute to complete disintegration of the tablets.

Figure 4:
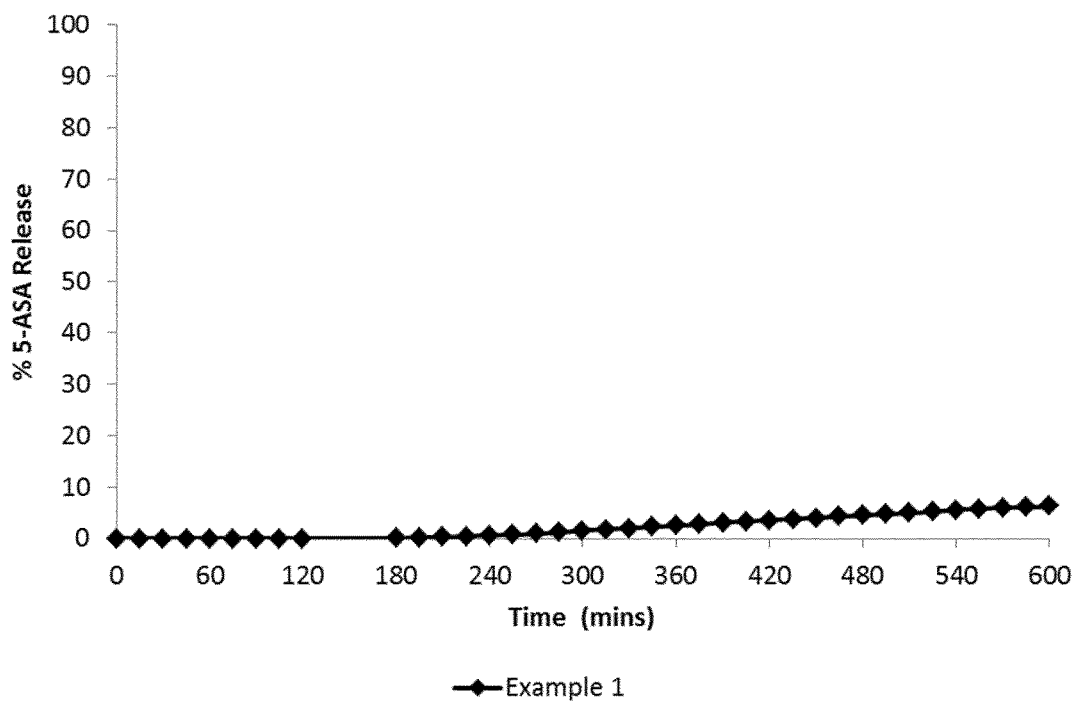
FIG. 4 is a graph depicting drug release as a function of time from 400 mg 5ASA tablets coated with an inner layer of fully neutralised Eudragit® S and an outer layer of a 30:70 mixture of starch and Eudragit® S (Example 1), when exposed to Hanks buffer at pH 6.8.

The Inventors have also observed that less than 10% of 5ASA is released from tablets of Example 1 when exposed to aqueous solution at pH 6.8 for 24 hours (see drug release test #4; FIG. 4). This result demonstrates the requirement for the presence of colonic enzymes in the surrounding medium to achieve significant release of the active from tablets according to the present invention and the resistance to the conditions of the small intestine, thereby efficiently preventing premature drug release.

Accelerated drug release under colonic conditions is also observed for formulations of the present invention where the inner layer comprises neutralised Eudragit® L30D-55 and the outer layer comprises a 30:70 mixture of starch/Eudragit® S 100 when compared with equivalent formulations in which the inner layer has not been neutralised. As indicated in FIG. 5, no release is observed from either formulation when exposed to 0.1 M HCl for 2 hours. However, when exposed to Krebs buffer at pH 7.4, initial release from the formulation according to the present invention (Example 2) is observed after 30 minutes whereas initial release from the comparative formulation (Comparative Formulation 4) does not occur until about 150 minutes. Similar acceleration of initial release is observed when these formulations are exposed to faecal slurry at pH 6.5 with initial release from the tablets having the neutralised inner layer (Example 2) taking place after about 2 hours in contrast to about 4 hours for the tablets with the non-neutralised inner layer (Comparative Example 4) (FIG. 6).

Formulations according to the present invention also demonstrate a clear advantage over the formulation exemplified in U.S. Pat. No. 5,422,121. In this regard, the Inventors reproduced as closely as possible the formulation of Example 2 of U.S. Pat. No. 5,422,121 in which a tablet core was coated first with an inner layer of Eudragit® L30D and then with an outer layer of a 1:3 mixture of Eudragit® L30D and guar gum (Comparative Example 5), and compared drug release over time in different conditions from this formulation with an equivalent formulation in which the Eudragit® L30D of the inner layer was fully neutralised according to one embodiment of the present invention (Example 3). Under all of the colonic conditions tested, initial drug release was accelerated for the formulation having the neutralised inner layer (see FIGS. 7 to 9).

Formulations having an inner layer comprising a non-ionic polymer, a base and a buffer agent also demonstrate accelerated initial drug release when compared with equivalent formulations in which the inner layer does not contain a base or a buffer agent. In this regard, the Inventors have demonstrated that initial release may be reduced from 4 hours to 3 hours when exposed to Krebs buffer in embodiments having an inner PVA polymer layer and an outer layer comprising a 70:30 mixture of Eudragit® S/Eudragit® FS (50:50) blend and starch, provided that the inner layer contains a base and a buffer agent (FIG. 10).

Incomplete drug release was observed in some of the test runs after 10 hours at colonic conditions (see in particular FIGS. 8 and 9). The Inventors note that this observation may be explained by the fact that high dosage (1200 mg) tablets were tested in these runs and sink conditions could not be achieved with the low capacity buffers (Krebs and Hanks buffers) used, or with the limited volume (210 ml) of faecal slurry used.

In contrast, the tablets of Examples 5 to 7 do not exhibit significant release prematurely when exposed to the simulated fed state conditions over the duration of the test (FIGS. 11, 14, 15). In addition, the tablets of Example 7 do not demonstrate a significant "food effect" when exposed to the simulated fed and fasted states over the duration of the tests (FIG. 15). In other words, not only do these tablets demonstrate less than 10% drug release by the end of the tests, but the release profiles in both the simulated fed and fasted states are either very similar (Example 7; FIG. 15) or almost identical (Example 6; FIG. 14).

The results appear to support the conclusion a food effect associated with coated 5ASA tablets may be reduced or even eliminated by providing the tablets with a coating according to the present invention. In particular, the results appear to indicate that applying the outer coating using a "semi organic" coating preparation rather than an aqueous coating preparation can eliminate the food effect (Example 1; FIG. 16).

It can be seen therefore that the delayed release formulation according to the present invention is significantly superior to comparative formulations.

Whilst the invention has been described with reference to a preferred embodiment, it will be appreciated that various modifications are possible within the spirit or scope of the invention as defined in the following claims.

In this specification, unless expressly otherwise indicated, the word 'or' is used in the sense of an operator that returns a true value when either or both of the stated conditions is met, as opposed to the operator 'exclusive or' which requires that only one of the conditions is met. The word 'comprising' is used in the sense of 'including' rather than in to mean 'consisting of'. All prior teachings acknowledged above are hereby incorporated by reference. No acknowledgement of any prior published document herein should be taken to be an admission or representation that the teaching thereof was common general knowledge in Australia or elsewhere at the date hereof.

The invention claimed is:

1. A delayed release drug formulation for oral administration to deliver a drug to the colon of a subject, said formulation comprising:
   a core and a coating for the core, the core comprising a drug and the coating comprising an outer layer and an inner layer,
   wherein the outer layer comprises a mixture of a first polymeric material which is susceptible to attack by colonic bacteria and a second polymeric material which has a pH threshold at about pH 6 or above,
   wherein the inner layer comprises a third polymeric material which is soluble in intestinal fluid or gastrointestinal fluid, said third polymeric material being a polycarboxylic acid polymer selected from the group consisting of polymethacrylate; cellulose acetate phthalate (CAP); polyvinyl acetate phthalate (PVAP); hydroxypropyl methylcellulose phthalate (HPMCP); hydroxypropyl methylcellulose acetate succinate (HPMC-AS); xanthan gum; and shellac,
   wherein said polycarboxylic acid polymer is at least partially neutralized such that at least 90% of the carboxylic acid groups are in the form of carboxylate anions, and
   wherein the at least partially neutralized polycarboxylic acid polymer is the sole film-forming polymer in the inner layer.

2. The formulation of claim 1, wherein said polycarboxylic acid polymer is fully neutralized.

3. The formulation of claim 1, wherein said second polymeric material is based on the same polycarboxylic acid polymer as said third polymeric material, and the third polymeric material has a higher degree of neutralization than the second polymeric material.

4. The formulation of claim 1, wherein said third polymeric material is an at least partially neutralized co-polymer of (meth)acrylic acid and a (meth)acrylic acid $C_{1-4}$ alkyl ester.

5. The formulation of claim 1, wherein said third polymeric material is a fully neutralized co-polymer of (meth)acrylic acid and (meth)acrylic acid methyl ester.

6. The formulation of claim 1, wherein the second polymeric material is a blend of at least two different polymers having a pH threshold of about pH 5 and above.

7. The formulation of claim 6, wherein the at least two different polymers in the blend are different polymethacrylate polymers.

8. The formulation of claim 6, wherein there are two different polymers in the blend in a weight ratio from about 40:60 to about 60:40.

9. The formulation of claim 1, wherein the first and second polymeric materials are present the outer layer in a weight ratio of up to about 60:40.

10. The formulation of claim 1, wherein the first and second polymeric materials are present in the outer layer in a weight ratio from about 25:75 to about 35:65.

11. The formulation of claim 1, wherein the first and second polymeric materials are present in the outer layer in a weight ratio from about 40:60 to about 60:40.

12. A method of producing the delayed release drug formulation for oral administration to deliver a drug to the colon as claimed in claim 1, said method comprising:
   forming the core comprising the drug;
   coating the core with an inner coating preparation comprising the third polymeric material in a solvent system to form an inner coated core; and
   coating the inner coated core with an outer coating preparation comprising the first polymeric material and the second polymeric material to form an outer coated core.

13. The method of claim 12, wherein the solvent system of the inner coating preparation is aqueous.

14. The method of claim 12, wherein said third polymeric material is said polycarboxylic acid polymer that is at least partially neutralized, said method comprising dispersing a polycarboxylic acid polymer in a solvent, optionally with the buffer agent, and adding the base to at least partially neutralize the polycarboxylic acid polymer to form the inner coating preparation.

15. The method of claim 14, wherein the amount of base added is at least sufficient to neutralize at least 10% of the carboxylic acid groups in the polycarboxylic acid polymer.

16. The method of claim 14, wherein the amount of base added is more than sufficient to fully neutralize the polycarboxylic acid polymer.

17. The method of claim 12, wherein said third polymeric material is said non-ionic polymer, the pH of the inner coating preparation being adjusted prior to coating to be at least 0.5 pH units higher than the pH threshold of the second polymeric material.

18. The method of claim 12, wherein the pH of the inner coating preparation is adjusted to be from about pH 7.5 to about pH 10.

19. The method of claim 12, wherein the base is selected from the group consisting of hydroxide bases, alkali metal bicarbonates, alkali metal carbonates, alkali metal phosphates, alkali metal citrates, or physiologically tolerated amines.

20. The method of claim 12, wherein the base is a hydroxide.

21. The method of claim 12, wherein the base is sodium hydroxide.

22. The formulation of claim 6, wherein there are two different polymers in the blend in a weight ratio of about 50:50.

23. The formulation of claim 1, wherein the first and second polymeric materials are present in the outer layer in a weight ratio of about 30:70.

24. The formulation of claim 1, wherein the first and second polymeric materials are present in the outer layer in a weight ratio of about 50:50.

25. The formulation of claim 1, wherein said inner layer further comprises at least one additive selected from the group consisting of a buffer agent, which is a non-polymeric organic acid or an inorganic salt, and a base, which is a non-polymeric base.

26. The formulation of claim 25, wherein the inner layer comprises the buffer agent and the base.

27. The formulation of claim 25, wherein the inner layer comprises a buffer agent and wherein the buffer agent is selected from the group consisting of a carboxylic acid having from 1 to 16 carbon atoms, an alkali metal salt, an alkali earth metal salt, an ammonium salt and a soluble metal salt.

28. The formulation of claim 25, wherein the inner layer comprises a buffer agent and wherein the buffer agent is a phosphate salt.

29. The formulation of claim 25, wherein the inner layer comprises a buffer agent and wherein the buffer agent is potassium dihydrogen phosphate.

30. The formulation of claim 25, wherein the inner layer comprises a buffer agent and wherein the buffer agent is present in the inner layer an amount from about 0.1 wt % to about 20 wt % based on the dry weight of the third polymeric material.

31. The formulation of claim 25, wherein the inner layer comprises a base and wherein the base is selected from the group consisting of hydroxide base, alkali metal bicarbonate, alkali metal carbonate, alkali metal phosphate, alkali metal citrate, and physiologically tolerated amine.

32. The formulation of claim 25, wherein the inner layer comprises a base and wherein the base is a hydroxide base.

33. The formulation of claim 25, wherein the inner layer comprises a base and wherein the base is sodium hydroxide.

* * * * *